(12) United States Patent
Hargittai et al.

(10) Patent No.: US 12,053,384 B2
(45) Date of Patent: *Aug. 6, 2024

(54) BUFFER FOR FEMORAL HEAD AND NECK EXCISION

(71) Applicant: IDR-BIOMED LTD, Orpington (GB)

(72) Inventors: Tamir Hargittai, Orpington (GB); Haim Geva, London (GB)

(73) Assignee: IDR-BIOMED LTD, Orpington (GB)

( * ) Notice: Subject to any disclaimer, the term of this patent is extended or adjusted under 35 U.S.C. 154(b) by 720 days.

This patent is subject to a terminal disclaimer.

(21) Appl. No.: 17/091,176

(22) Filed: Nov. 6, 2020

(65) Prior Publication Data

US 2021/0121294 A1 Apr. 29, 2021

Related U.S. Application Data

(63) Continuation-in-part of application No. 15/553,460, filed as application No. PCT/GB2016/050481 on Feb. 25, 2016, now Pat. No. 10,828,167.

(30) Foreign Application Priority Data

Feb. 27, 2015 (GB) ..................................... 1503291

(51) Int. Cl.
*A61F 2/32* (2006.01)
*A61F 2/30* (2006.01)
(Continued)

(52) U.S. Cl.
CPC ............ *A61F 2/34* (2013.01); *A61F 2/30771* (2013.01); *A61F 2/3609* (2013.01);
(Continued)

(58) Field of Classification Search
CPC .. A61F 2/34; A61F 2/36; A61F 2/3603; A61F 2/4607; A61F 2/30749; A61F 2/32; A61F 2/30771; A61F 2/3609; A61F 2002/3432; A61F 2002/3401; A61F 2002/30578; A61F 2002/30576
See application file for complete search history.

(56) References Cited

U.S. PATENT DOCUMENTS 3,740,769 A * 6/1973 Haboush ................... A61F 2/32
623/22.36
4,467,479 A 8/1984 Brody
(Continued)

FOREIGN PATENT DOCUMENTS

DE 102008017014 A1 10/2009
WO 2011091004 A2 7/2011

OTHER PUBLICATIONS

International Search Report and Written Opinion for International Application No. PCT/GB2016/050481, mailed Aug. 10, 2016 (15 pages).
(Continued)

*Primary Examiner* — Seema Mathew
(74) *Attorney, Agent, or Firm* — Kagan Binder, PLLC

(57) ABSTRACT

An apparatus for the treatment of canine or other animal hip pathologies, the apparatus (200) comprising a buffer (210) adapted to be disposed between a femur (10) and a hip socket (25), and a fixing means (250) adapted to fix the buffer to the femur.

18 Claims, 23 Drawing Sheets

(51) Int. Cl.
*A61F 2/34* (2006.01)
*A61F 2/36* (2006.01)
*A61F 2/46* (2006.01)

(52) U.S. Cl.
CPC ...... *A61F 2/4607* (2013.01); *A61F 2002/307* (2013.01); *A61F 2002/3082* (2013.01); *A61F 2002/3401* (2013.01); *A61F 2002/3432* (2013.01); *A61F 2002/3435* (2013.01); *A61F 2002/3621* (2013.01)

(56) References Cited

U.S. PATENT DOCUMENTS

| | | | |
|---|---|---|---|
| 4,502,161 A * | 3/1985 | Wall | A61F 2/30756 606/907 |
| 5,314,490 A * | 5/1994 | Wagner | A61F 2/34 623/22.36 |
| 5,549,692 A * | 8/1996 | Hauser | A61F 2/30734 623/22.3 |
| 5,609,646 A * | 3/1997 | Field | A61F 2/34 623/22.32 |
| 6,004,353 A * | 12/1999 | Masini | A61F 2/34 623/22.21 |
| 6,056,777 A | 5/2000 | McDowell | |
| 6,110,211 A | 8/2000 | Weiss | |
| 6,740,120 B1 | 5/2004 | Grimes | |
| 7,611,653 B1 | 11/2009 | Elsner et al. | |
| 7,799,077 B2 | 9/2010 | Lang et al. | |
| 8,403,985 B2 | 3/2013 | Hodorek | |
| 8,617,242 B2 | 12/2013 | Philipp | |
| 8,828,089 B1 * | 9/2014 | Perez | A61F 2/30734 623/22.21 |
| 9,757,241 B2 | 9/2017 | Grotz | |
| 9,808,345 B2 * | 11/2017 | Grotz | A61F 2/32 |
| 9,839,523 B1 | 12/2017 | Foran | |
| 2002/0143402 A1 | 10/2002 | Steinberg | |
| 2004/0006393 A1 | 1/2004 | Burkinshaw | |
| 2006/0009853 A1 | 1/2006 | Justin et al. | |
| 2006/0085080 A1 | 4/2006 | Bechgaard et al. | |
| 2006/0235517 A1 | 10/2006 | Hodorek | |
| 2006/0241758 A1 | 10/2006 | Peterman et al. | |
| 2007/0129809 A1 | 6/2007 | Meridew et al. | |
| 2008/0051889 A1 * | 2/2008 | Hodorek | A61F 2/30756 623/18.11 |
| 2009/0088846 A1 | 4/2009 | Myung et al. | |
| 2009/0187252 A1 | 7/2009 | Howald et al. | |
| 2009/0226068 A1 | 9/2009 | Fitz et al. | |
| 2009/0259314 A1 | 10/2009 | Linder-Ganz et al. | |
| 2010/0010114 A1 | 1/2010 | Myung et al. | |
| 2010/0023126 A1 | 1/2010 | Grotz | |
| 2010/0198274 A1 | 8/2010 | Yeung et al. | |
| 2011/0288642 A1 | 11/2011 | Forsell | |
| 2013/0018479 A1 | 1/2013 | Grotz | |
| 2013/0123929 A1 * | 5/2013 | McDaniel | A61F 2/40 623/19.13 |
| 2014/0031948 A1 | 1/2014 | Birmingham | |
| 2014/0316526 A1 | 10/2014 | Grotz | |
| 2015/0135907 A1 * | 5/2015 | Hirabayashi | B23Q 5/048 81/54 |
| 2015/0342740 A1 | 12/2015 | Boedo et al. | |
| 2018/0344465 A1 | 12/2018 | McPherson et al. | |
| 2021/0121294 A1 * | 4/2021 | Hargittai | A61F 2/36 |
| 2024/0082010 A1 * | 3/2024 | Servidio | A61F 2/30771 |

OTHER PUBLICATIONS

Search Report for GB Application No. GB1503291.5, mailed Jul. 27, 2015 (3 pages).

\* cited by examiner

Fig. 10A
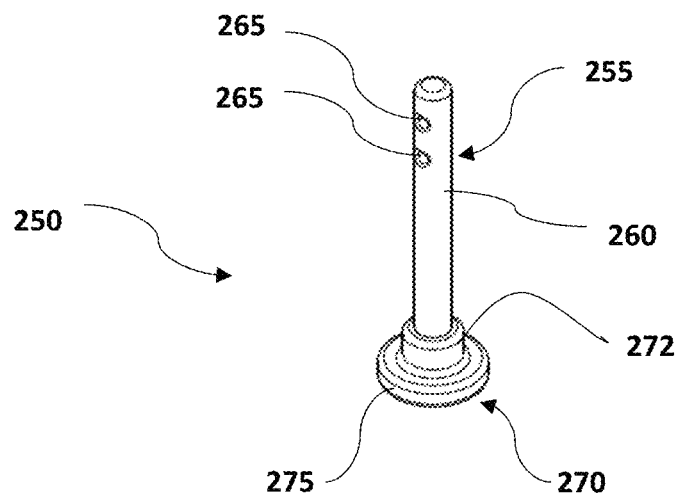
Fig. 10B
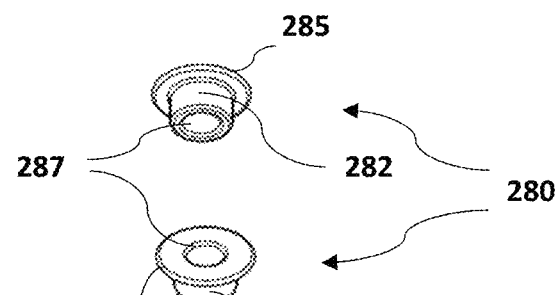
Fig. 10C
Fig. 10D
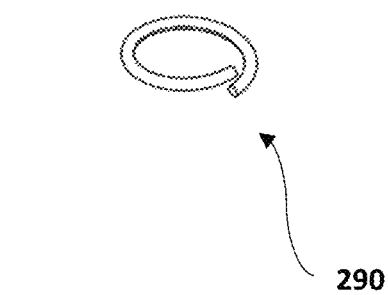

BUFFER FOR FEMORAL HEAD AND NECK EXCISION

CROSS-REFERENCE TO RELATED APPLICATIONS

This application is a Continuation-in-Part of U.S. patent application Ser. No. 15/553,460, filed Aug. 24, 2017, now allowed, which claims benefit from International Application No. PCT/GB/2016/050481, filed Feb. 25, 2016, which in turn claims priority from Great Britain Application having serial number 1503291.5, filed on Feb. 27, 2015, all of which are incorporated herein by reference in their entireties for all purposes.

FIELD

The present invention relates to apparatus and methods for treatment of hip joint, femoral head and femoral neck problems, particularly in canines but also in other animals.

BACKGROUND

Dogs and other animals commonly suffer pain and/or disability associated with hip pathology, such as arthritis, which may be secondary to hip dysplasia, traumatic hip luxation, and fractures of the femoral head or neck that do not have a good prognosis following surgical repair. Owners desire to treat animals suffering these conditions.

There are currently three common ways of dealing with such hip pathology. The first is conservative (non-surgical) management of the disease and symptoms, which is by far the most common way of managing the condition. However, such treatment is often not effective in relieving pain and mobility dysfunction, and these cases would ideally benefit from surgical treatment.

The second is to perform a total hip replacement which, if successful, is considered to have the most close resemblance to, and be closest to restoration of natural hip biomechanics. FIG. 1 shows a healthy canine hip joint, in which the head 15 of the femur 10 is fitted in the acetabulum or hip socket 25 of the pelvis 20. The femoral neck 17 is between the femoral head 15 and the remaining part of the femur 10. In a total hip replacement, as shown in FIG. 2, the femoral neck 17 and head 15 are excised and the hip socket 25 is reamed out. The head 15 is replaced with a new prosthetic ball 35 and the hip socket 25 is replaced with a prosthetic socket 40. In particular, with most such implants, a cylindrical hole is drilled out of the femur 10 and a metal stem 30 is inserted in the hole and fixed with pins, force fit or cement 37. The ball 35 is fixed to the stem 30. Usually, at least the ball is made of metal, and is rigid and carefully formed with a high dimensional accuracy. In addition, a plastic cup inside a metal cover 40 is fitted to the pelvis 20 using a screw 47, bone cement or a self-tapping design and the ball 35 is fitted in the cup 40. There are a number of variations in femoral stem and acetabular cup insertion and fixation techniques on the market.

However, whilst being considered a very good surgical treatment, a total hip replacement involves difficult and expensive surgery, and whilst complication rates are relatively low (5-15%) a total hip replacement has the potential for very serious complications (septic and aseptic implant loosening, dislocation, femoral fracture, nerve damage) often requiring major revision surgeries and high associated additional costs to an already costly procedure. Therefore, the operation is almost exclusively an orthopedic specialist procedure and can rarely be undertaken by general practitioner vets. It is time consuming and requires the use of expensive implants and expensive dedicated surgical tools. Consequently, a total canine hip replacement costs many thousands of pounds, which is often not affordable for most pet owners. Moreover, the operation is often deemed less suitable for some dogs, in particular those regarded as higher risk (old, debilitated, concurrent health problems), and those that cannot be restricted in exercise for several months by their owners for a variety of reasons, till healing has occurred.

An alternative to total hip replacement is resurfacing of the femoral head 15. This involves attaching a cup-shaped prosthesis to the exterior of the femoral head 15. However, there may be difficulties in sizing the prosthesis so that it fits closely enough to the femoral head. Moreover, the procedure may still require replacement of the hip socket 25 with a prosthetic hip socket 40.

The third common way of dealing with hip pathology is to perform femoral head and neck excision. This involves removing the femoral head 15 and neck 17, without inserting any prostheses in their place. The aim is to relieve joint pain by eliminating the joint, with the compromise of losing normal hip biomechanics. In practice, a dog that has undergone this procedure will hold its weight on its muscles. A well-recognized problem is variable degrees of bone-to-bone contact post operatively, that is mitigated to a degree by interposing scar tissue that forms over time between the cut surface and the pelvis.

A femoral head and neck excision is a relatively straightforward procedure that can be carried out by most non-specialist vets. In addition, it is relatively quick and does not require any special parts. It also does not require restricting exercise after surgery, on the contrary it is encouraged from day one. As such, it is considerably cheaper than a total hip replacement and can usually be performed for under £1,000. Thus, the procedure is well suited for dogs whose owners are unable or unwilling to spend the considerable sums required for a total hip replacement or femoral head resurfacing, unwilling to undertake the risks and additional costs of severe complications or are unable to restrict exercise, and for other dogs not otherwise suited to a total hip replacement or femoral head resurfacing. Consequently, femoral head and neck excisions are more commonly performed than total hip replacements.

However, a femoral head and neck excision is not without disadvantages, as has clearly been demonstrated in several published studies. Often long term, but particularly in the early days after the operation, the dog will experience painful bone to bone contact, therefore limiting its willingness to use the leg, which is very important in preventing long term reduction in range of motion. The operation also shortens the leg. Moreover, the subsequent development of interposing scar tissue will usually not entirely prevent bone to bone contact so the dog experiences residual pain. The scar tissue also limits the range of motion of the dog. Thus, the dog will put less weight on the leg on which the operation has been performed, the dog will have limited movement and the dog will continue to experience discomfort. These symptoms tend to be more evident in heavier dogs, although they have been shown to be present similarly in smaller dogs.

Where there are severe complications in total hip replacements and no further operation is possible, the prostheses may be removed, having the same end effect as simply performing a femoral head and neck excision. In a similar way, if femoral head/socket resurfacing is unsuccessful, the prostheses may be removed and femoral head and neck excision performed.

SUMMARY OF THE INVENTION

Accordingly, the known surgical methods of treatment of hip pathology, especially arthritis, in canines and other animals are either insufficiently effective or are too expensive and with possible severe complications and therefore not suited for many dogs. The present invention has been made to address these problems.

According to a first aspect of the present invention, there is provided an apparatus for the treatment of a hip, the apparatus comprising: a buffer adapted to be fitted to an excision surface of a femur from which at least the femoral head has been excised and to be disposed between a femur and at least a part of a pelvis around a hip socket; and a fixing means adapted to fix the buffer to the femur.

In this specification, the expression 'a part of a pelvis around a hip socket' may include the rim of the acetabular socket.

Preferably, the buffer comprises a resilient material to abut at least a part of the pelvis around the hip socket.

Preferably, the buffer has a curved top surface adapted to abut at least a part of the pelvis around the hip socket.

Preferably, the buffer has a substantially flat bottom surface adapted to abut the excision surface.

Preferably, the buffer comprises a first part to be fitted to the excision surface and arms extending from opposite sides of the first part, the arms having arm holes for attaching the arms to the sides of the femur.

More preferably, an axis of the arm holes is substantially parallel to a bottom of the first part.

It is also more preferable that the apparatus further comprises a pin for extending between the arm holes through a hole provided in the femur.

Yet more preferably, one or more fixing holes extends through the pin at an angle to the longitudinal axis of the pin, the one or more fixing holes being provided towards a distal end of the pin.

It is also more preferable that the apparatus further comprises a sleeve adapted to fit over the distal end of the pin.

It is further preferable that the sleeve has a plate-like portion suitable for being interposed between a fixing wire and the femur.

More preferably, a proximal end of the pin has a larger diameter than a shaft of the pin.

It is also more preferable that the apparatus further comprises a plate like portion at a proximal end of the pin and arranged to abut the femur when the apparatus is mounted to the femur.

According to another aspect of the invention, there is provided a drill guide for drilling a hole in a femur for mounting an apparatus according to any one of the preceding claims, the drill guide comprising: a first part for abutting an excision surface; and drill guide arms extending from opposite sides of the first part, the arms having drill guide holes for guiding drilling.

Preferably, the drill guide further comprises a drill guide pin mountable to one of the drill guide holes.

More preferably, the drill guide pin can be screwed into the said drill guide hole whereby the drill guide arms compress the femur.

It is also more preferably that a distal tip of the drill guide pin is shaped to grip or bite the femur.

Preferably, at least one of the drill guide arms is provided with a serrated or roughened surface for gripping the femur.

Preferably, the drill guide holes are formed further from the first part than corresponding attachment arm holes are from the corresponding first part of the buffer.

According to another aspect of the invention, there is provided a buffer for use in an apparatus as described above.

According to another aspect of the invention, there is provided a kit comprising an apparatus and a drill guide both as described above.

According to another aspect of the invention, there is provided a method for treatment of a hip joint comprising: drilling a hole into a femur from which a femoral head has been excised; and fitting a buffer to an excision plane, the buffer adapted to abut at least a part of a socket of the hip joint.

Preferably, the hole is spaced apart from the excision plane.

More preferably, the hole extends through the femur.

Preferably, the drilling comprises: mounting a drill guide according to any one of claims 13 to 18 to the excision plane; screwing a drill guide pin to a drill guide hole, thereby compressing arms of the drill guide against the femur; and moving a drill bit through the drill guide pin prior to drilling into the femur.

The present invention includes a buffer, apparatus, kit, drilling guide or method as herein described with reference to the whole or any part of the description and all or any one or more of the drawings.

In another aspect of the invention, there is provided an apparatus for the treatment of a hip, the apparatus comprising: a buffer adapted to be disposed between a femur and at least a part of a pelvis around a hip socket; a bone screw adapted to fix the buffer to the femur.

Preferably, the buffer has a curved top surface adapted to abut at least a part of the pelvis around the hip socket.

Preferably, the buffer has a substantially flat bottom surface adapted to abut a surface of a femur from which at least the femoral head has been excised.

Preferably, the bone screw has a flat head with an aperture therein shaped to receive a screwdriver of a complementary shape.

Preferably, the buffer is adapted to be press-fitted on a head of the bone screw.

Preferably, the apparatus further comprises an integration screw for fixing the buffer to the bone screw.

In this case, it is preferred that the buffer comprises an aperture, a bottom part of the aperture sized to fit over a head of the bone screw, an upper part of the aperture sized to fit a head of the integration screw and a middle part of the aperture sized to fit a shaft of the integration screw, whereby the buffer can be fixed between the bone screw and the integration screw.

It is also preferred in this case that the integration screw has a flat head with an aperture therein shaped to receive a screwdriver of a complementary shape.

It is also preferred in this case that the integration screw has a magnetic head.

Preferably, the apparatus further comprises an anchor screw for preventing rotation of the buffer about the bone screw relative to the femur.

In this case, it is preferred that the buffer comprises an anchor screw aperture, an upper part of the anchor screw aperture sized to fit a head of the anchor screw and a lower part of the anchor screw aperture sized to fit a shaft of the anchor screw, whereby the anchor screw can be screwed into the femur.

Preferably, the buffer comprises an aperture to be fitted over a head of the bone screw and the head of the bone screw and the aperture are sized and shaped so as to prevent rotation relative to one another about a longitudinal axis of the bone screw.

According to another aspect of the present invention, there is provided an apparatus according to any one of the preceding claims and a drilling template showing positions to be drilled for the bone screw and the anchor screw.

According to another aspect of the present invention, there is provided a method for treatment of a hip joint comprising: fixing a bone screw to a femur from which a femoral head has been excised; and fitting a buffer to the bone screw, the buffer adapted to abut at least a part of a socket of the hip joint.

Preferably, the method further comprises using an integration screw to fix the buffer to the bone screw.

Preferably, the method further comprises excising the femoral head and drilling a hole for fixing the bone screw to the femur.

Preferably, the method further comprises using an anchor screw to fix the buffer to the femur independently of the bone screw.

In this case, it is preferred that the method further comprises drilling a hole for fixing the anchor screw to the femur.

According to another aspect of the present invention there is provided a buffer of the apparatus or method as described above.

BRIEF DESCRIPTION OF THE DRAWINGS

Embodiments of the present invention will now be described by way of example only with reference to the accompanying drawings, in which:

FIGS. 10A-D are perspective views of a fixing mechanism forming part of the apparatus of the second embodiment;

DETAILED DESCRIPTION

The present invention provides a buffer between the cut surface 11 of a femur 10 and the existing acetabulum 25 and adjacent pelvic bone. This eliminates the painful bone-to-bone abrasion that can be a major source of pain and discomfort, thereby facilitating much earlier return to function (critical to a good end result) as well as long term prevention of discomfort due to this reason. This also reduces scar tissue adherence to the stump and thus reduces the reduction in range of motion. In this way, some of the major problems of the existing femoral neck and head excision treatment can be substantially mitigated or eliminated without the expense and risk of undertaking total hip replacement. Furthermore, the rate and severity of complications with the present invention is potentially much lower than a total hip replacement, as this present novel implant minimises the forces born by the screw and practically eliminates stress shield.

Figure 1:
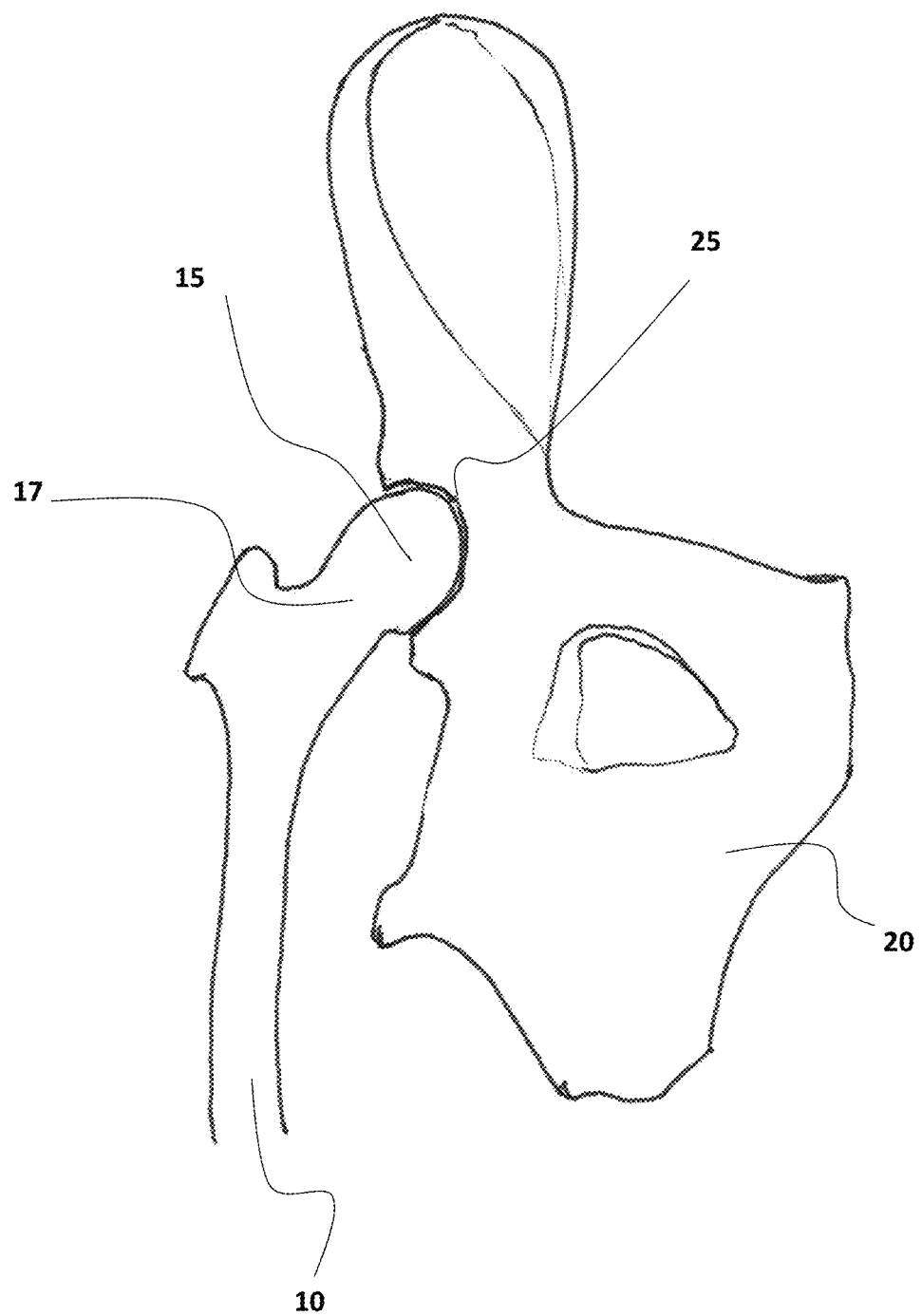
FIG. 1 is an illustration of a healthy canine hip joint.
Figure 2:
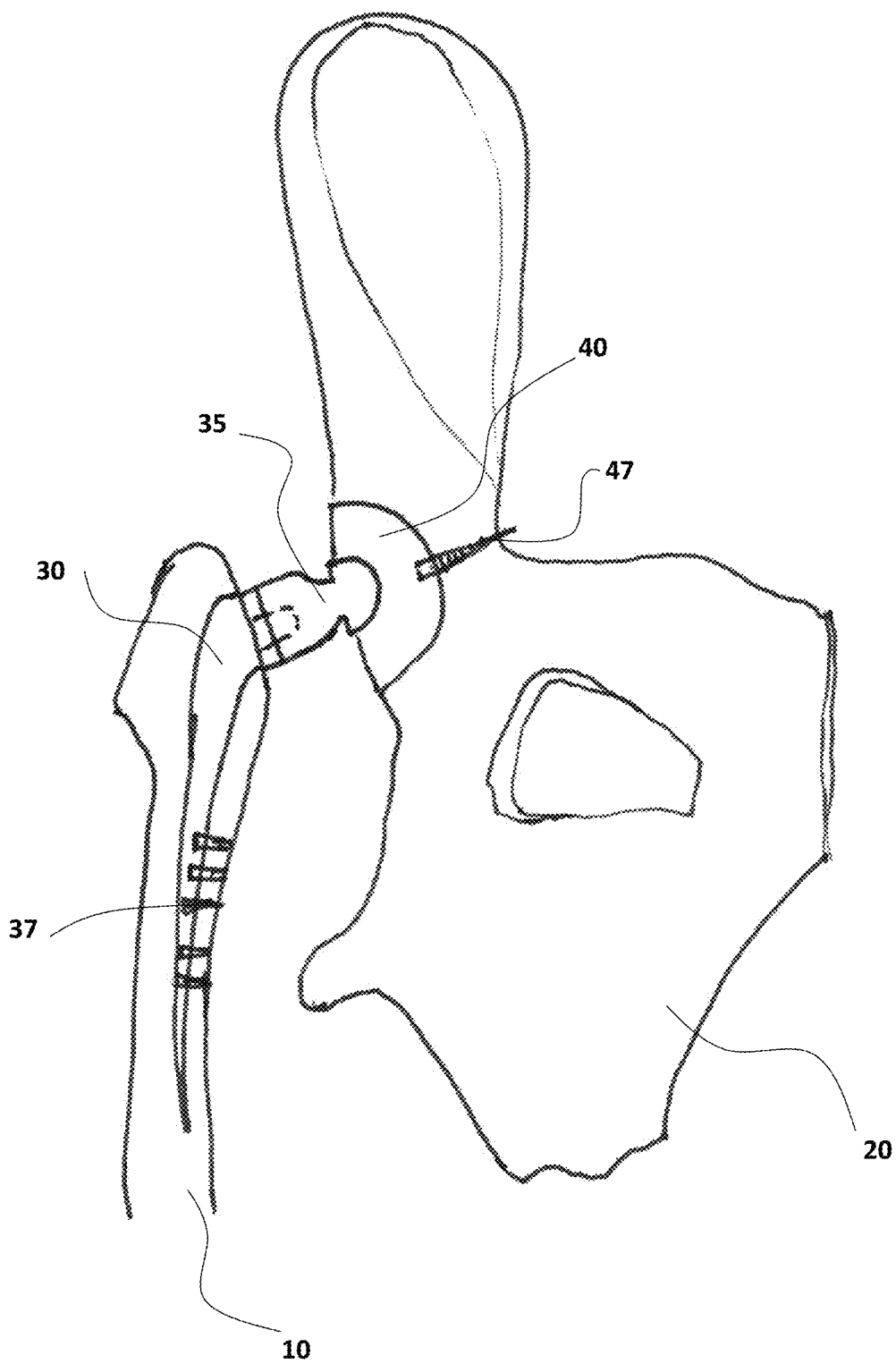
FIG. 2 is an illustration of a total hip replacement as known in the prior art.
Figure 3A:
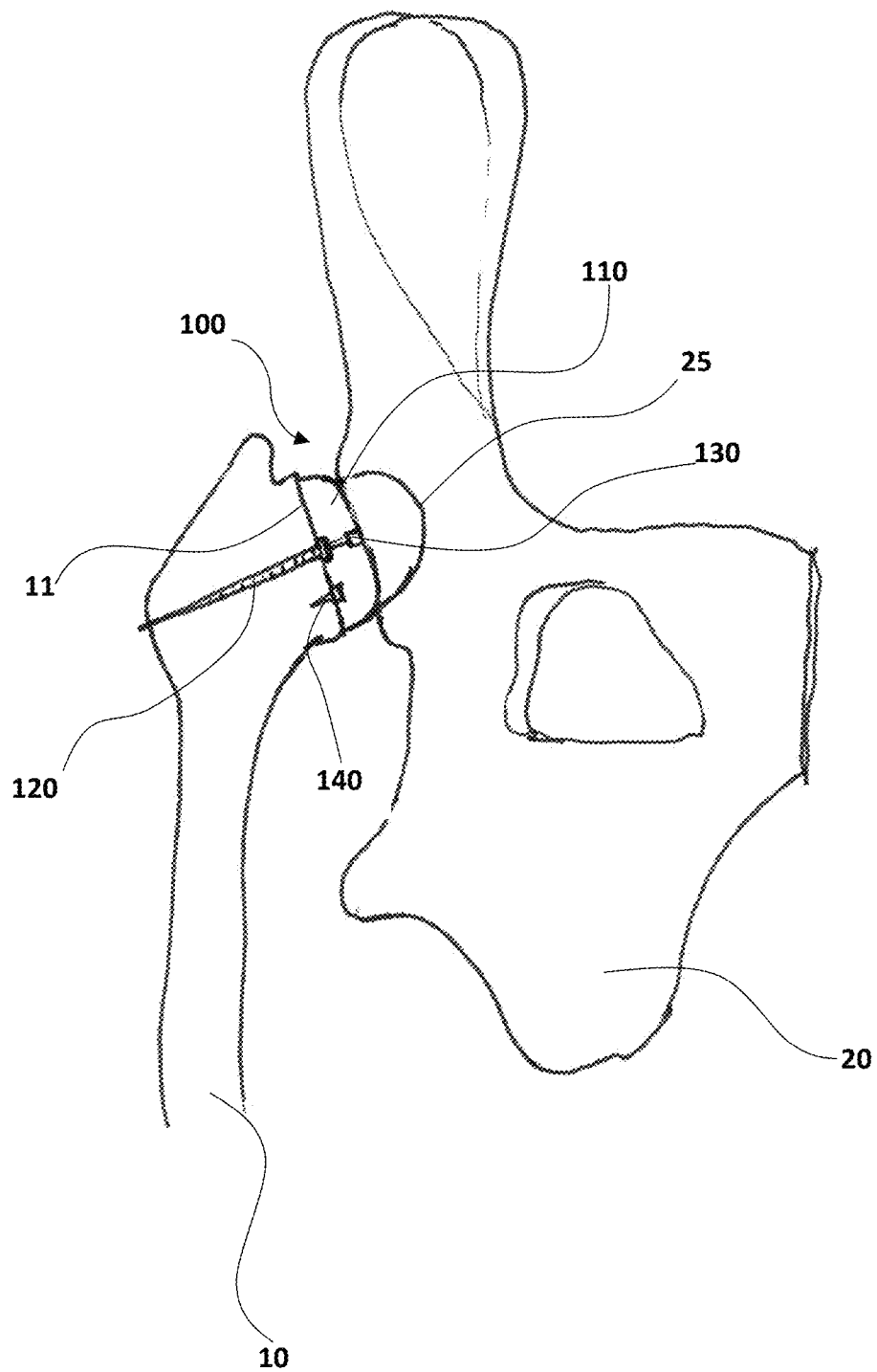
FIG. 3A is an illustration of a hip treatment apparatus according to a first embodiment of the present invention.
Figure 3B:
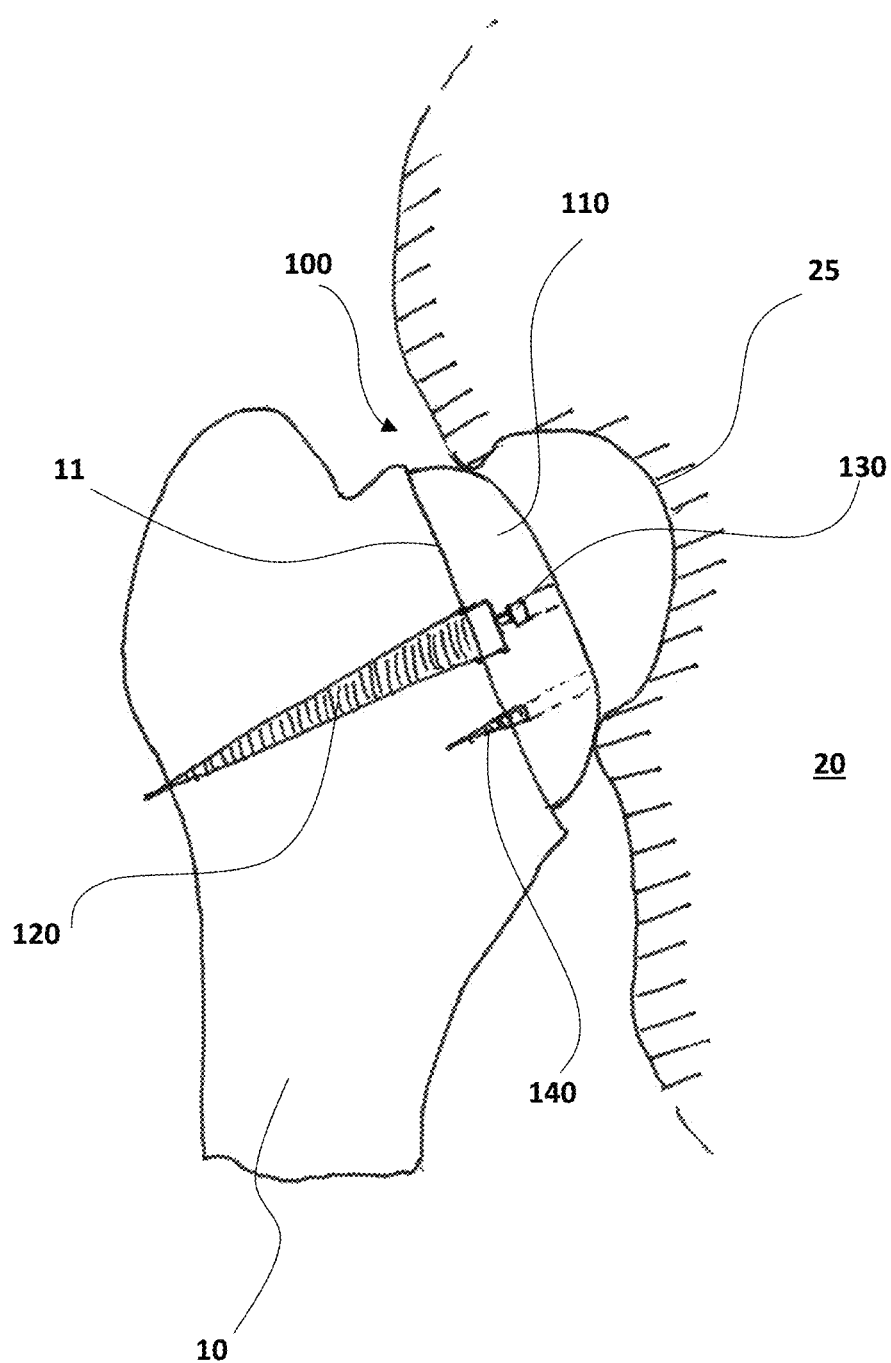
FIG. 3B is a close up of a portion of FIG. 3A.

FIGS. 3A and 3B show a first embodiment of the present invention. In the embodiment, an apparatus 100 is attached to a femur 10 that has undergone, for example, a femoral head and neck excision to provide a substantially planar surface 11. The apparatus 100 comprises a cushion 110, which acts as the buffer, a bone screw 120 to which the cushion 110 is mounted, an integrating screw 130 to more firmly secure the cushion 110 to the head 126 of the bone screw, and an anchor screw 140 to prevent lateral or rotational movement of the cushion 110 relative to the femur. The cushion is entirely made of or includes a resilient material. The bottom 118 of the cushion 110 is flat and covers all or most of the planar surface 11 of the femur 10. The top 116 of the cushion 110 is curved to provide a smooth, rounded, low profile on the upper surface (see FIGS. 4A and 4B). The top of the cushion 110 abuts the outside of socket 25 of pelvis. The perimeter of the cushion 110 at its largest point is larger than that of the opening to the socket 25 and therefore it sits outside the socket and contacts the rim of the acetabular socket and pelvic bone at various levels during weight bearing range of motion 25, as shown in FIGS. 3A and B.

The provision of the buffer (in this embodiment in the form of a cushion 110) between the cut surface of the femur 10 and the existing hip socket 25 prevents bone to bone contact, and in particular prevents the femur 10 from scraping the interior and the rim of the socket 25 or any other part of the pelvis 20, thereby significantly relieving pain and therefore enabling early return to function which is critical in achieving a long-term good functional outcome. In addition, the provision of the buffer reduces scar tissue formation, and this ensures that the range of motion of the femur 10 relative to the pelvis 20 does not become substantially restricted.

Figure 5A:
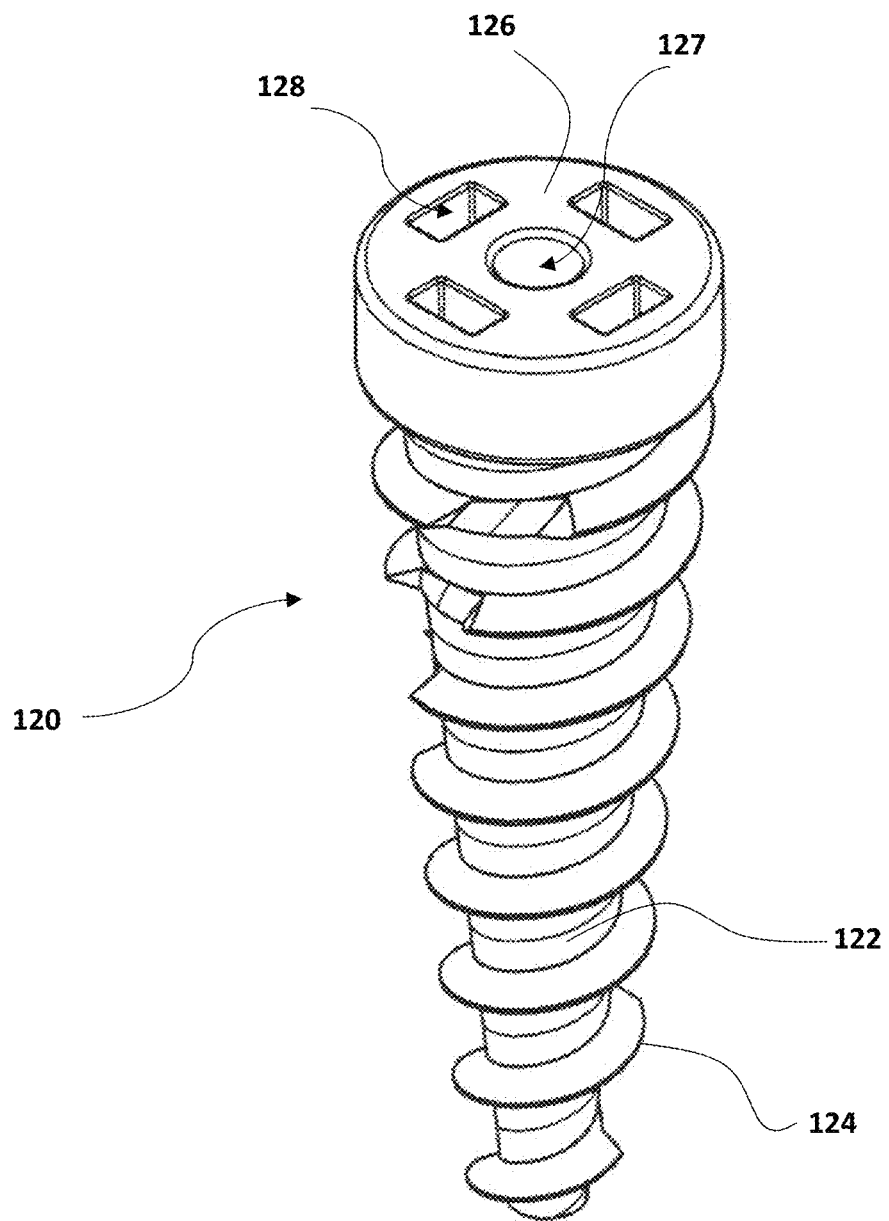
FIG. 5A is a perspective view of a bone screw forming part of the apparatus of the first embodiment.
Figure 5B:
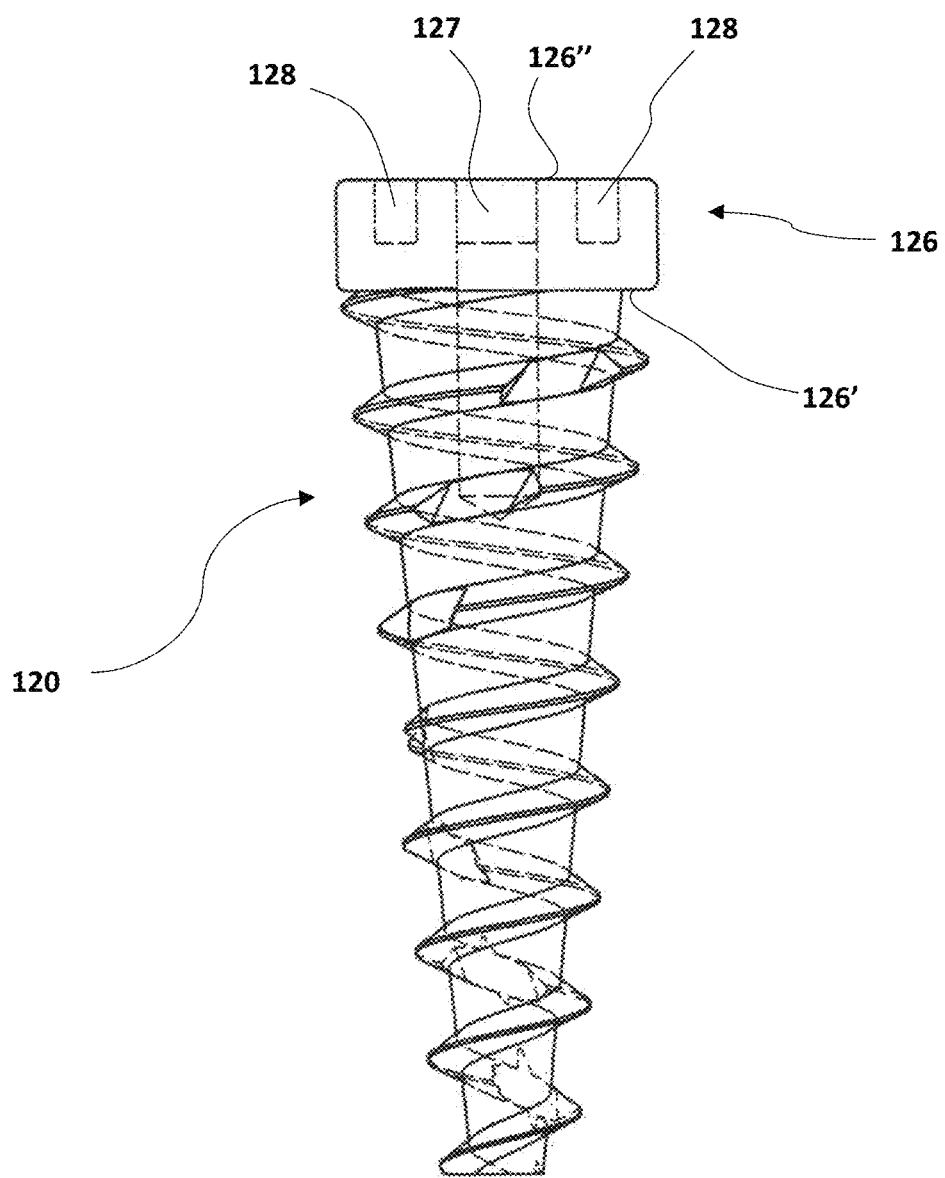
FIG. 5B is a side view of the bone screw.

The respective components of the apparatus 100 will now be described in more detail. FIGS. 5A and 5B show an isometric view and a side view of the bone screw 120 respectively. As shown in these figures, the bone screw 120 includes a head 126 and a shaft 122 with thread 124. The shaft 122 is preferably conical or frustoconical and the thread 124 is self-tapping. The head 126 is circular in plan view. It has a flat bottom portion 126', which abuts against the planar cut surface 11 when the bone screw 120 is fitted, and a flat top 126". Four rectangular indentations 128 are provided in the top 126", although the indentations may have other shapes and be different in number. In addition, a hole 127 is provided in the middle of the top 126" into which the integration screw 130 (described later) can be inserted. Preferably the hole 127 is threaded, although other methods of fixation may be used.

The bone screw 120 can take any suitable dimensions. By way of example, however, the full height of the bone screw 120 from top 126" of the head 126 to the bottom of the shaft 122 may be approximately 31.5 mm; the distance between the top 126" and bottom 126' of the head 126 about 3.5 mm; the diameter of the head 126 about 10 mm; the hole 127 for the integration screw about 10 mm deep and 2.5 mm in diameter; and each of the indentations 128 about 2 mm deep. Any suitable thread geometry and dimensions may be used as is known in the art.

The bone screw 120 is preferably made of or with polyether ether ketone (PEEK) or the like, which has a similar modulus to that of bone and therefore reacts to and is displaced by a load in a similar manner to bone. By contrast, if the bone screw 120 is made of metal, which is more rigid, then the surrounding bone is vulnerable to fracture and osteoporosis. In preferred embodiments, the thread 124 is coated with porous titanium or hydroxylapatite to stimulate bone growth onto the thread.

Figure 6A:
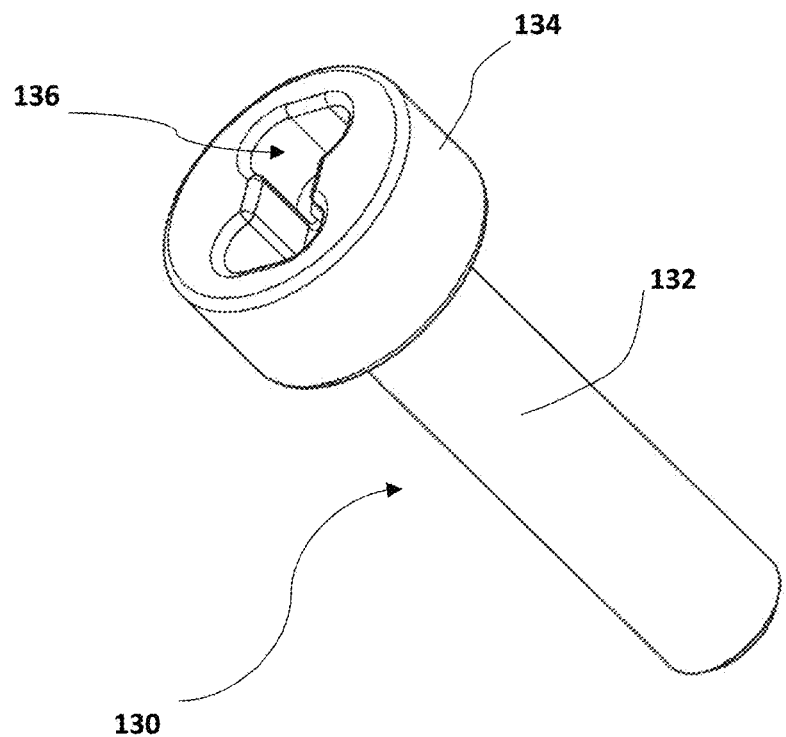
FIG. 6A is a perspective view of an integration screw forming part of the apparatus of the first embodiment.
Figure 6B:
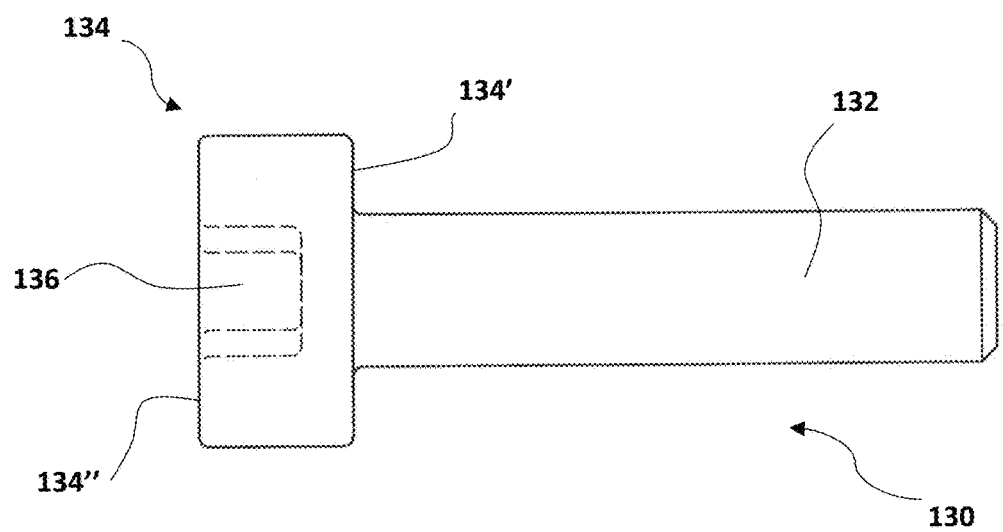
FIG. 6B is a side view of the integration screw.

The integration screw 130 is shown in FIGS. 6A and B. It comprises a shaft 132 and a head 134. Although not shown, the shaft 132 is preferably threaded to match the thread of the hole 127 in the bone screw 120, as will be discussed later. Alternatively, the diameter of the shaft may be sized to be press-fitted into the hole 127. The head 136 preferably has a flat bottom 136' and a flat top 136" and also includes a butterfly-, dog bone- or similar-shaped indentation 136.

The integration screw 130 can take any suitable dimensions. By way of example, however, the full height of the integration screw 130 from the top 134" of the head 134 to the bottom of the shaft may be approximately 15.5 mm; the distance between the top 134" and the bottom 134' of the head 134 about 3 mm; the diameter of the head 134 about 6 mm; and the indentation 136 about 2 mm deep. The integration screw 130 is also preferably made of PEEK.

Figure 4A:
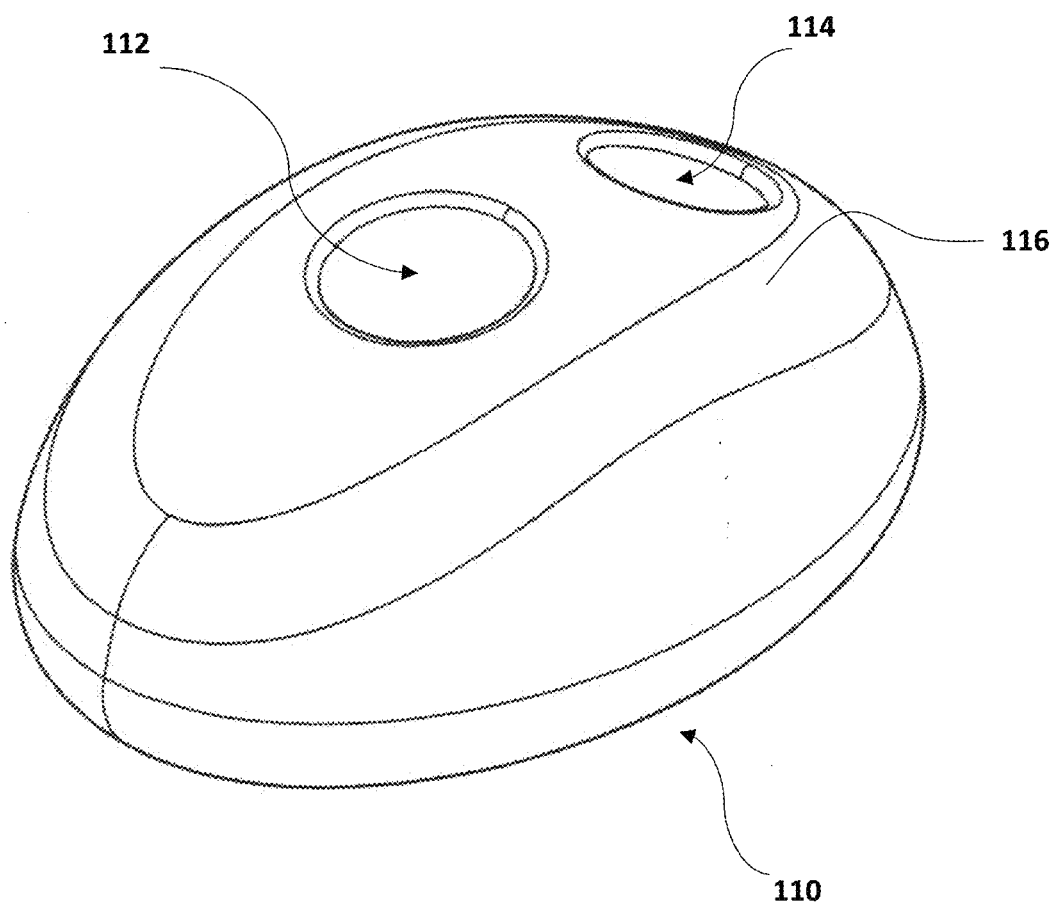
FIG. 4A is a perspective view of a cushion forming part of the apparatus of the first embodiment.
Figure 4B:
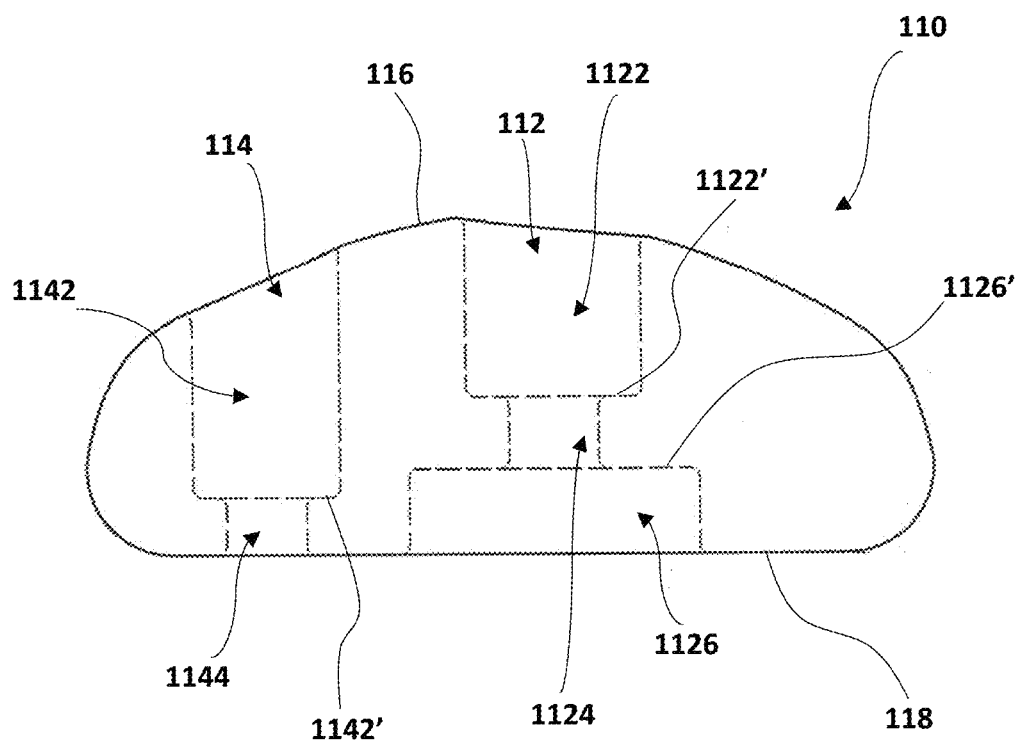
FIG. 4B is a side view of the cushion.
Figure 4C:
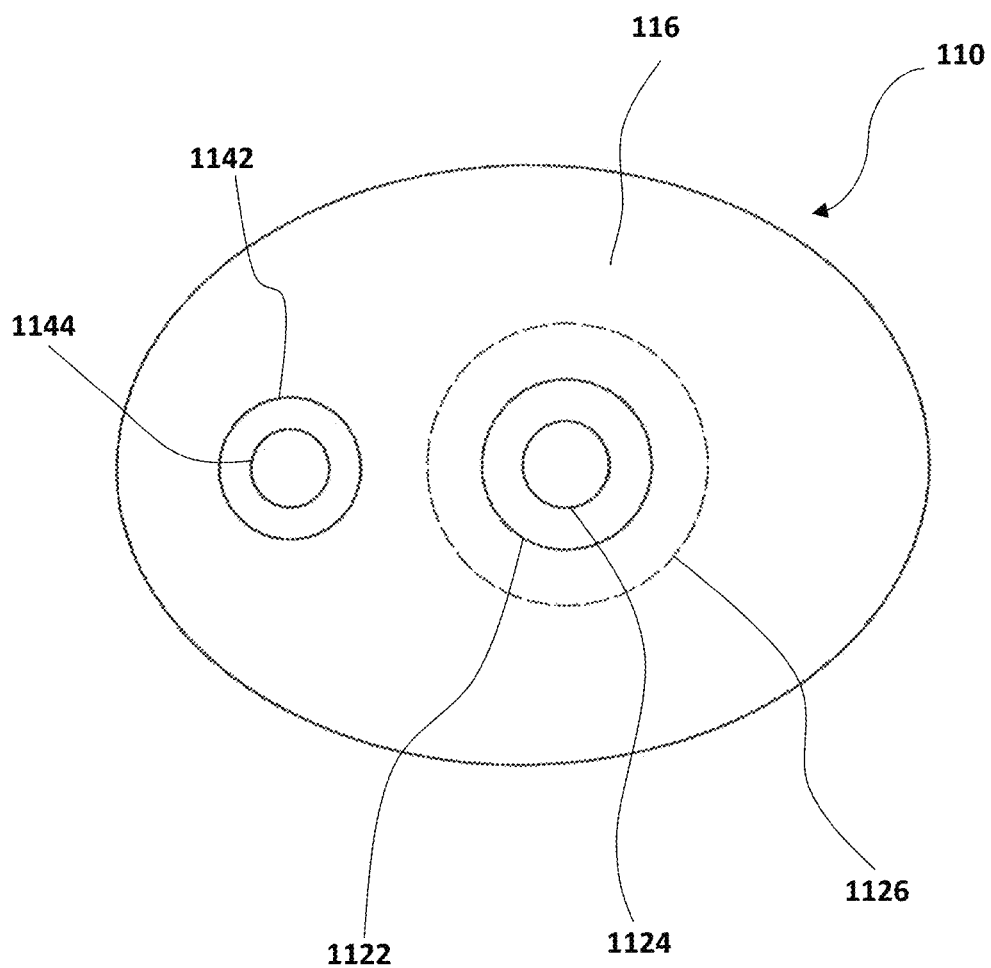
FIG. 4C is a top view of the cushion.

FIGS. 4A-C show details of the cushion 110. Preferably the cushion 110 is moulded as a single piece of polyurethane rubber, which is a biocompatible resilient material. Other materials may also be used so long as the cushion 110 acts to buffer movement of the femur 10 relative to the pelvis 20 and particularly to the socket 25 thereby relieving pain from bone to bone contact.

In plan view (see FIG. 4C), the cushion has a substantially oval shape substantially to match the shape of the cut surface 11 of the femur 10. As shown in FIGS. 4A-C, apart from the flat bottom 118, the cushion 110 has rounded surfaces all over to prevent sharp edges contacting the femur 10 or the pelvis 20 (including the socket 25) to minimise pain. The rounded surfaces of the cushion may include sections with different radii of curvature blended together or joined together by sections that are flat when viewed in one or more directions. The resulting smooth, low, rounded profile ensures the cushion can abut the outer rim of the socket 25 and allows it to move easily relative to the socket 25.

The cushion 110 includes an aperture 112 for the bone screw 120 and the integration screw 130 and another aperture 114 for the anchor screw 140, which will be described later. The apertures may have rounded rims where they meet the top surface 116 and the bottom surface 118 to further reduce sources of pain.

As shown in FIGS. 4B and 4C, the aperture 112 has three sections 1122, 1124 and 1126, from top to bottom, of different diameters. All sections 1122, 1124, 1126 share the same longitudinal axis, although this is not essential. The diameter of the bottom section 1126 is sized to be press-fitted over the head 126 of the bone screw 120. After press-fitting, the flat top 126" of the head 126 of the bone screw 120 abuts the bottom step 1126' between the middle and bottom sections 1124 and 1126 of the aperture 112 and the bottom 126' of the head 126 of the bone screw 120 lines in substantially the same plane as the bottom 118 of the cushion 110. The top and middle sections 1122 and 1124 of the aperture 112 are sized to allow the integration screw to fit through. Thus, the shaft 132 of the integration screw 130 can be passed through the middle section 1124 and screwed/press-fitted into the hole 127 of the bone screw 120 until the bottom 134' of the head 134 of the integration screw 130 abuts the top step 1122' between the top and middle sections 1122 and 1124 of the aperture 112. In this manner, the cushion 110 can be more securely fitted to the bone screw 120.

The aperture 114 for the anchor screw 140 has two sections 1142 and 1144 from top to bottom. These sections 1142, 1144 share the same longitudinal axis, although again this is not essential. In a similar manner to the top and middle sections 1122 and 1124 of the aperture 112, these sections 1142 and 1144 are sized so that both the shaft and head (not shown) of the anchor screw 140 can pass through the top section 1142 and only the shaft of the anchor screw 140 can pass through the bottom section 1144. Thus, the anchor screw 140 can be passed through the aperture 114 and screwed into the femur 10 until the head of the anchor screw abuts the step 1142'. This serves to provide a point of anchoring of the cushion 110 relative to the femur 10. Since the anchor screw 140 has a different longitudinal axis to the bone screw 120, it prevents rotational movement of the cushion 110 relative to bone screw 120, and also helps to prevent lateral movement of the cushion relative to the femur 10. However, it is the fixing of the bone screw 120 to the femur 10 and the cushion 110 to the bone screw that acts as the principal way of fixing the cushion 110 to the femur 10.

The cushion 110 can take any suitable dimensions. By way of example, however, the maximum length of the cushion when viewed in plan view from the top (up down direction in FIG. 4C) may be about 29.5 mm; the maximum length of the flat bottom 118 up to the start of curvature about 23.5 mm; the maximum width when viewed in plan view from the top (left right direction in FIG. 4C) about 21.5 mm; the maximum width of the bottom 118 about 15.5 mm; the maximum height from the top 116 to the bottom 118 about 12 mm; the depth of the top section 1122 of the aperture 112 about 6 mm; the depth (total length) of the middle section 1124 of the aperture 112 about 2.5 mm; the depth (total length) of the bottom section 1126 of the aperture 112 about 3.5 mm; the diameter of the top section 1122 of the aperture 112 about 6 mm; the diameter of the middle section 1124 of the aperture 112 about 3 mm; the diameter of the bottom section 1126 of the aperture 112 about 10 mm; the diameter of the top section 1142 of the aperture 114 about 5 mm; the diameter of the bottom section 1144 of the aperture 114 about 3 mm; the depth (total length) of the bottom section 1144 of the aperture 114 about 2 mm; the shortest distance in the length direction in plan view (down direction in FIG. 4C) form the edge of the bottom section 1126 of the aperture 112 to the outer edge of the cushion about 8 mm; the shortest distance in the length direction in plan view (up direction in FIG. 4C) from the edge of the top section 1142 of the aperture 114 to the outer edge of the cushion about 3.5 mm; and the distance between the longitudinal axes of the aperture 112 and the aperture 114 about 10 mm.

In this specification, all dimensions of the embodiment have been rounded to the nearest 0.5 mm. However, in other preferred embodiments the dimensions may all be varied in proportion to one another. In alternative embodiments, they may be varied relative to one another. For example, the dimensions of the cushion 110 may be changed but the dimensions of one or more of the bone screw 120, the integration screw 130 and the anchor screw 140 may be retained, and the dimensions of the apertures 112 and 114 changed or retained accordingly. In addition, the distance between the apertures 112 and 114 may be retained or varied with size irrespective of changes in size of the various screws. In this way, a number of different apparatuses 100 of different sizes may be provided to suit different sized dogs, each apparatus coming as a kit of parts.

Although not shown in detail, the anchor screw 140 may be any suitable screw sized to fit into the anchor screw aperture 140 and be screwed into the femur 10 to provide the anchoring effect described above. Preferably, the anchor screw 140 is a self-tapping, stainless steel cancellous screw, although any suitable screw of any suitable material may be used.

To fit the apparatus 100, a vet or any suitably trained person first performs a femoral head and neck excision on the femur 10 of the affected hip joint to provide a planar cut surface 11. If a femoral head and neck excision has already been performed then this step can be omitted, or a new planar surface 11 can be cut as necessary. The position of the cut and the size of the apparatus 100 (or at least cushion 110) where different-sized apparatuses are provided can be selected to match the size of the femur 10. Alternatively, only the head 15 may be excised and the apparatus 100 can be attached to the remaining femoral neck 17.

Figure 7:
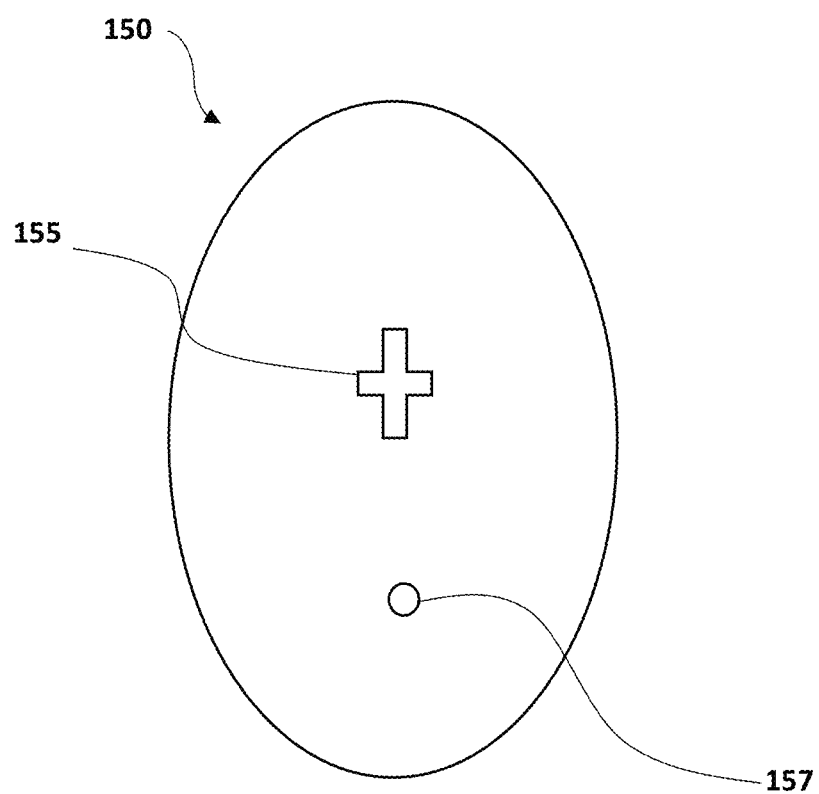
FIG. 7 shows a drilling template according to an aspect of the first embodiment of the invention.

Subsequently, the vet drills pilot holes in the cut surface 11 for the bone screw 120 and, preferably, the anchor screw 140. This can be done using a drilling template 150, as shown in FIG. 7. More specifically, the vet can place the template 150 against the cut surface 11, use the hole 155 to drill a pilot hole for the bone screw 120 and use the hole 157 to drill a pilot hole for the anchor screw 140. The vet then removes the template 150, and screws in the bone screw 120 until the bottom 126' of the head 126 of the bone screw 120 abuts the cut surface 11. This can be achieved using a screwdriver (not shown) having a head of complementary shape to the four indentations 128 in the head 126 of the bone screw 120. The screwdriver is then removed to provide a bone screw 120 firmly fixed to the cut surface 11 with a head 126 having a flat top 126".

Next, the vet press fits the bottom section 1126 of the aperture 112 of the cushion 110 over the head 126 of the bone screw 120 until the top 126" of the head 126 of the bone screw 120 and the step 1126' in the aperture 112 abut. The cushion 110 can be oriented so it is aligned with the cut surface 11 to cover or substantially cover it. In this way, the cushion 110 is attached and fixed to the bone screw 120. Thus, the bone screw 120 fixes the cushion 110 to the femur 10.

The vet then inserts the integration screw 130 into the top section 1122 of the aperture 112 of the cushion 110 and screws it into the hole 127 in the head 126 of the bone screw 120 until the bottom 134' of the head 134 of the integration screw 130 abuts the step 1122' in the aperture 112 of the cushion 110. This can be achieved using a screwdriver (not shown) having a head of complementary shape to the indentation 136 in the head 134 of the integration screw 130. In this way, the cushion 110 is more securely fixed to and integrated with the bone screw 120.

Optionally, the head 134 of the integration screw and the head of the screwdriver may be magnetic so that the integration screw does not get lost during fitting. This arrangement may also be used for the bone screw 120 and the corresponding screwdriver.

Finally, the vet screws a cancellous anchor screw 140 through the aperture 114 of the cushion 110 into the cut surface 11 until its head abuts the step 1142'. This more firmly anchors the cushion 110 in place on the femur 10 and particularly prevents the cushion 110 from rotating about the bone screw 120. The anchor screw 140 in combination with the bone screw 120 also serves to prevent the cushion 110 from moving laterally on the cut surface and from coming away from the cut surface.

After the apparatus 100 has been fixed to the femur 10, the femur 10 and socket 25 are arranged so that the cushion 110 faces or abuts the rim of the socket 25, and the wound is closed routinely.

Use of the apparatus 100 according to the present invention has a number of significant advantages.

The cushion 110 is positioned between the cut surface 11 of the femur 10 and the socket 25. The cushion encounters the acetabular rim and pelvis, as shown in FIGS. 3A and B. Thus, it can be said that the cushion 110 is disposed between the femur 10 and at least a part of the pelvis 20 around a hip socket 25. The basic biomechanics of the back leg and hip with the present invention are essentially the same as with a traditional femoral head and neck excision, but without the impediment of the bone to bone contact and excessive scar tissue formation. It will be understood therefore, that the cushion 110 can move away from the hip socket 25 and is not meant to engage it. Consequently, the cushion 110 prevents bone to bone contact between the femur 10 and the pelvis 20, thereby significantly relieving pain compared both to the previously existing arthritic condition or other hip pathology and to the standard femoral head and neck excision. Because the cushion 110 is formed of resilient material, such as polyurethane, this pain relieving effect of the present invention is a long-term one.

Moreover, the cushion 110 prevents scar tissue from forming over the cut surface 11 and between the cut surface 11 and the pelvis 20 generally. This ensures that the range of movement of the joint does not become restricted with time following the operation. In particular, movement is constrained by the muscles and tendons only and not by the socket 25 or by scar tissue.

Consequently, the simple procedure of fitting the apparatus 100 of the present invention provides significantly improved pain relief and range of movement, both immediately after the operation and permanently after the operation, compared to carrying out only a femoral head and neck excision.

Moreover, the procedure of fitting the apparatus 100 of the present invention is much easier and faster than performing a total hip replacement and can be carried out by most general practitioner vets without further specialist training. It does not require reaming the socket 25, or fitting a new cup 40 or ball 35. There is no need to use any fixing 47 in the pelvis 20 or a nail 30 and fixing pins 37 in the femur 10.

Importantly, as opposed to a total hip replacement femoral implant, there is no weight bearing load whatsoever on the femoral component of the present invention, which makes implant loosening highly unlikely and therefore complication rates very low. Consequently, the procedure of fitting the apparatus 100 of the present invention is more suited to a wider range of dogs than a total hip replacement, including older dogs and other dogs that might not survive, or might not survive for long after, total hip replacement surgery, or that may not be able to risk (or afford) potential complications of total hip replacement.

The apparatus 100 of the present invention is also considerably cheaper than the components required in a total hip replacement—the expensive and high precision ball, socket and nail are not necessary, and the screws 120, 130, 140 and cushion 110 of the apparatus can be mass produced in a range of different sizes comparatively cheaply. Thus, a procedure using the apparatus 100 of the present invention is much more affordable than a total hip replacement. This makes the procedure using the apparatus 100 of the present invention more worthwhile for a greater range of dogs and their owners.

It will be appreciated by those skilled in the art that many modifications can be made to the apparatus 100 overall and/or any one or more of the individual components whilst still achieving the benefit of the invention.

For example, there is no need for whole cushion 110 to be formed of resilient material. Rather, the cushion can be formed of different materials, only some of which are resilient and provide a cushioning effect. In this case, it is preferred that the parts of the buffer expected to abut bone, including the cut surface 11 and/or the rim of the socket 25 be formed of resilient or otherwise cushioning material. It is also possible to form the buffer 110 entirely of a rigid or substantially rigid material, such as PEEK or a thermoplastic like it.

Either or both the integration screw and the anchor screw can be dispensed with, so the buffer is simply fitted on to the bone screw (preferably by press fitting). Alternatively, the bone screw 120 may screw through an aperture provided in the buffer to fix it to the bone.

The head 126 of the bone screw 120 need not have a circular section when viewed in plan. Rather the head 126 can have any suitable shape. For example, the head may have a square or other suitable shape and the bottom section 1126 of the aperture 112 may have a corresponding shape so that rotation between the two is prevented. In this case, the anchor screw 140 is even less essential.

It should also be noted that the bottom section 1126 and the head 126 need not have corresponding shapes, or be press fitted together.

A second, preferred embodiment of the invention will now be described with reference to FIGS. 8-12.

Figure 8A:
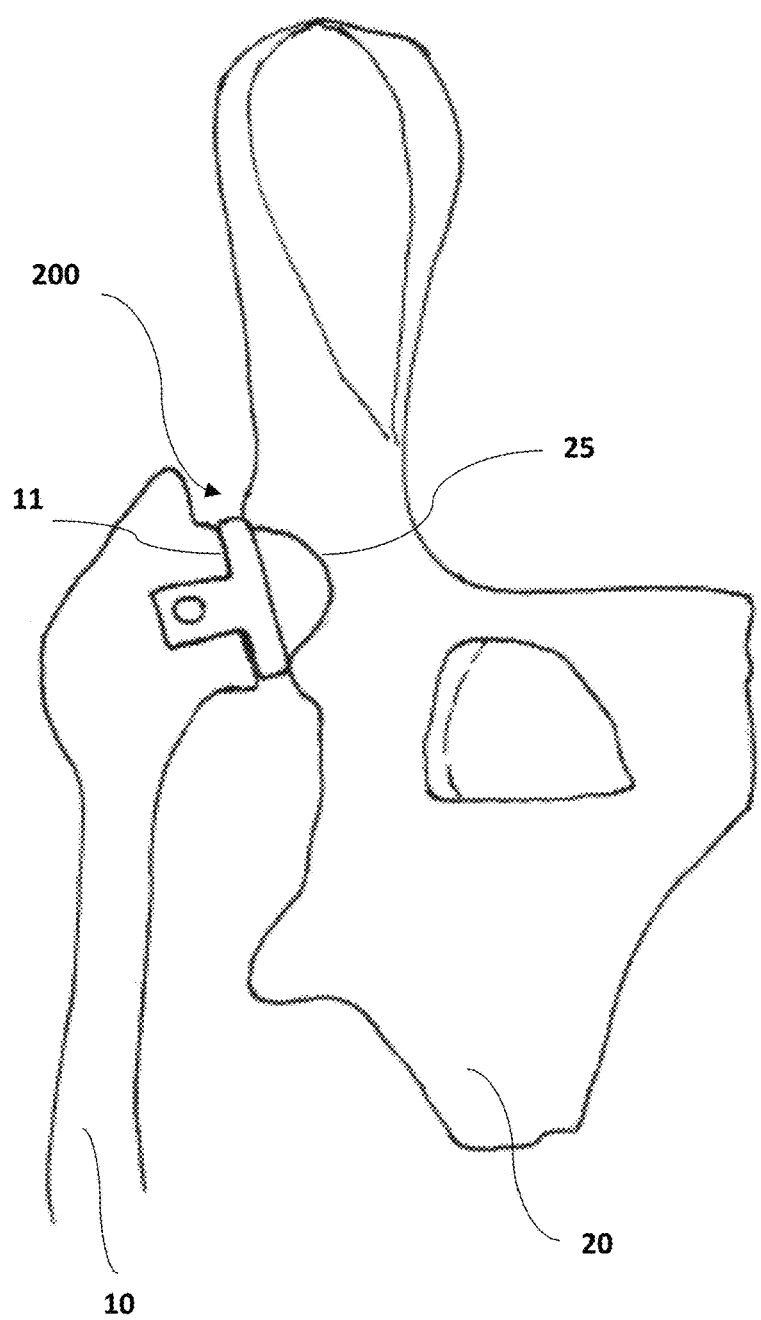
FIG. 8A is an illustration of a hip treatment apparatus according to a second embodiment of the present invention.
Figure 8B:
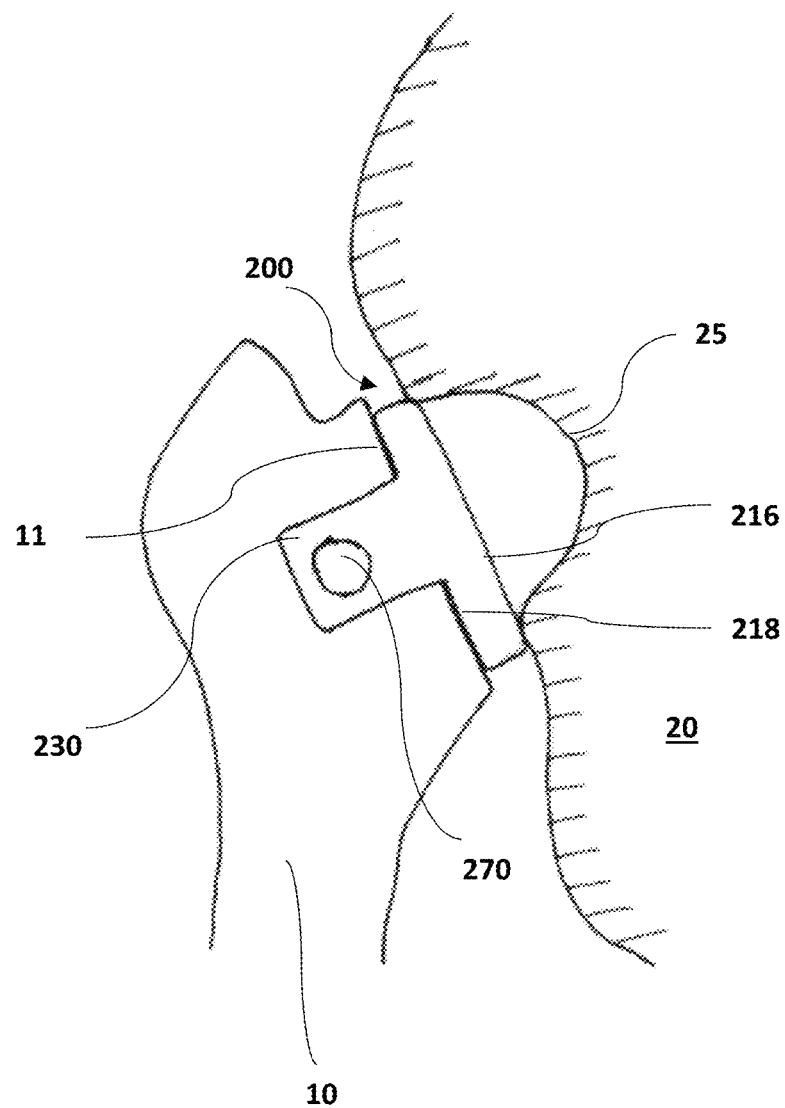
FIG. 8B is a close up of a portion of FIG. 8A.

As in the first embodiment, in the second embodiment an apparatus 200 is attached to a femur 10 that has undergone, for example, a femoral head and neck excision to provide the substantially planar surface 11. The apparatus 200 comprises a cover 210, which acts as the buffer, and pin 250 by which the cover 210 is mounted. The cover 210 is entirely made of or includes a resilient material. The cover 210 includes an upper part 214 and arms 230, 240. The bottom 218 of the upper part 214 is preferably flat and covers all or most of the planar surface 11 of the femur 10. The top 216 of the upper part 214 comprises a substantially flat upper surface 225, which is curved round at the edges 224 and corners 222 to provide a smooth, low profile with rounded edges on the top 216. This minimises the risk of damage to soft tissue in the vicinity of the cover 210. The top 216 of the upper part 214 abuts the outside of socket 25 of the pelvis 20. The perimeter of the upper part 214 at its largest point is larger than that of the opening to the socket 25 and therefore it sits outside the socket 25 and contacts the rim of the acetabular socket 25 and pelvic bone 20 at various levels during weight bearing range of motion, as shown in FIGS. 8A and 8B.

The provision of the buffer (in this embodiment in the form of a cover 210) between the cut surface 11 of the femur 10 and the existing hip socket 25 again prevents bone to bone contact, and in particular prevents the femur 10 from scraping the interior and the rim of the socket 25 or any other part of the pelvis 20, thereby significantly relieving pain and therefore enabling early return to function which is critical in achieving a long-term good functional outcome. In addition, the provision of the buffer 210 reduces scar tissue formation, and this ensures that the range of motion of the femur 10 relative to the pelvis 20 does not become substantially restricted.

Figure 9A:
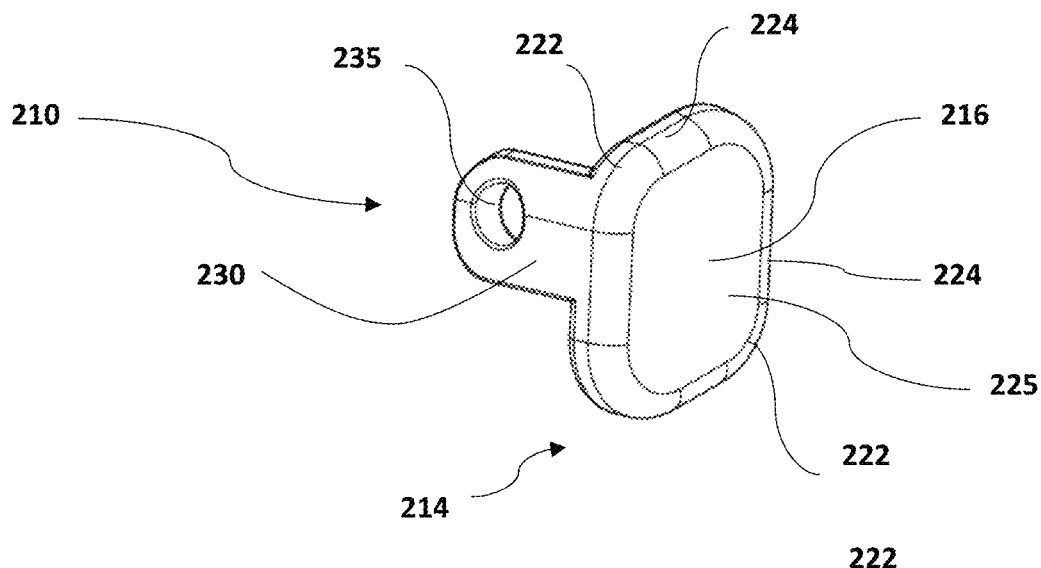
FIGS. 9A and B are perspective views of a cover forming part of the apparatus of the second embodiment.
Figure 9B:
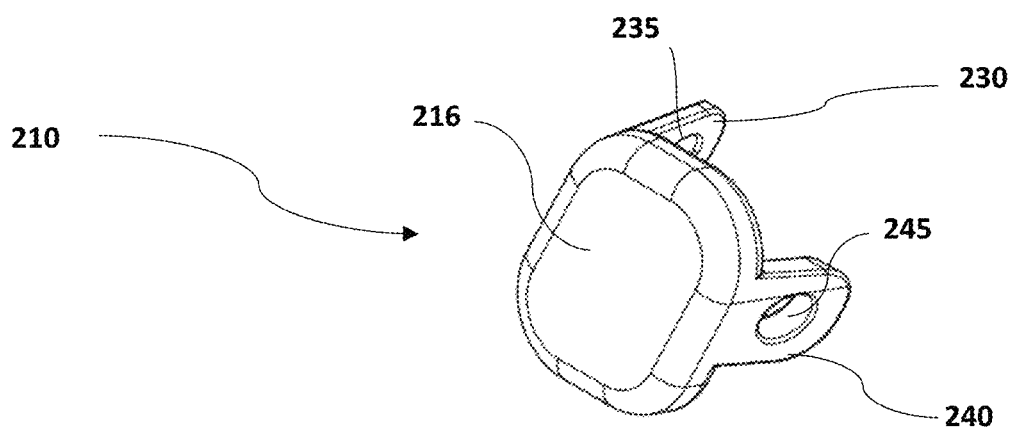
FIG. 9C is side elevation of the cover and FIG. 9D is a cross-sectional view as seen from the line E-E in FIG. 9C.
Figure 9C:
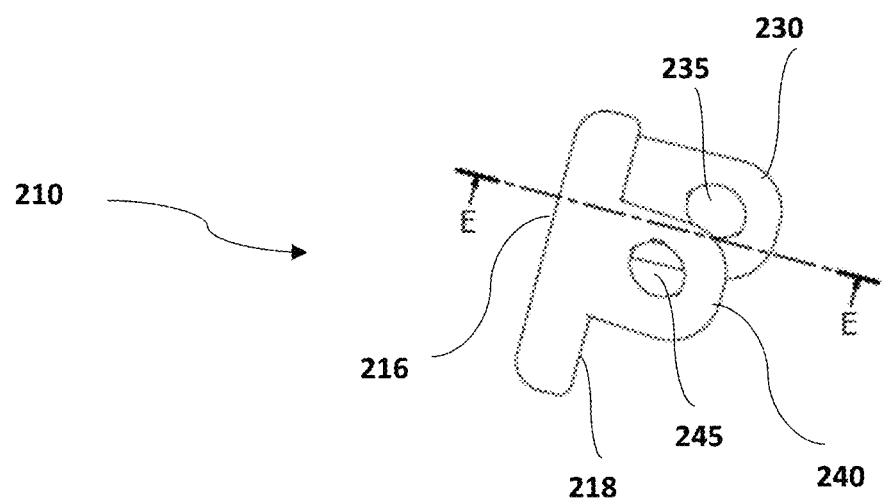
Figure 9D:
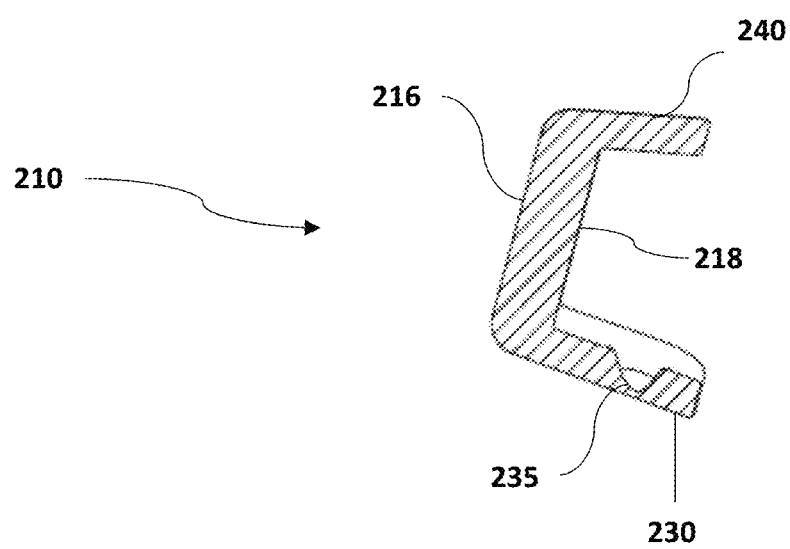
Figure 11A:
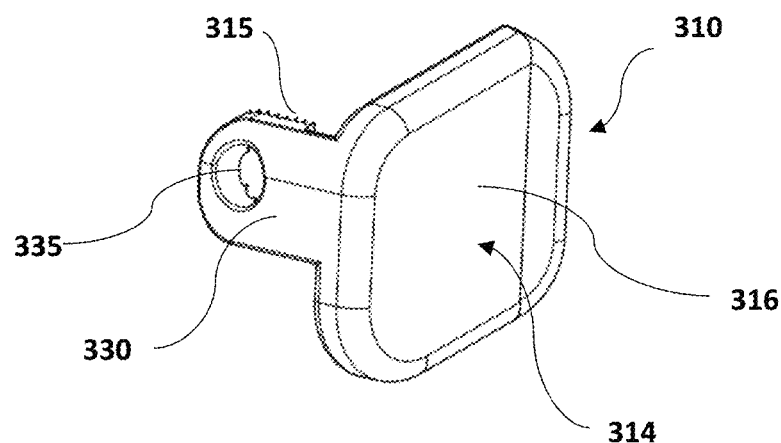
FIGS. 11A-C are perspective views of a drilling guide dummy according to an aspect of the second embodiment and FIG. 11D is a cross-sectional view as seen from the line C-C in FIG. 11C.
Figure 11B:
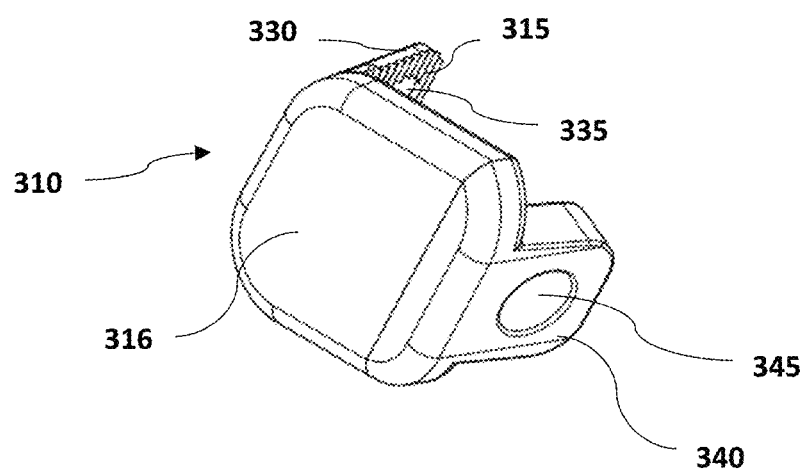
Figure 11C:
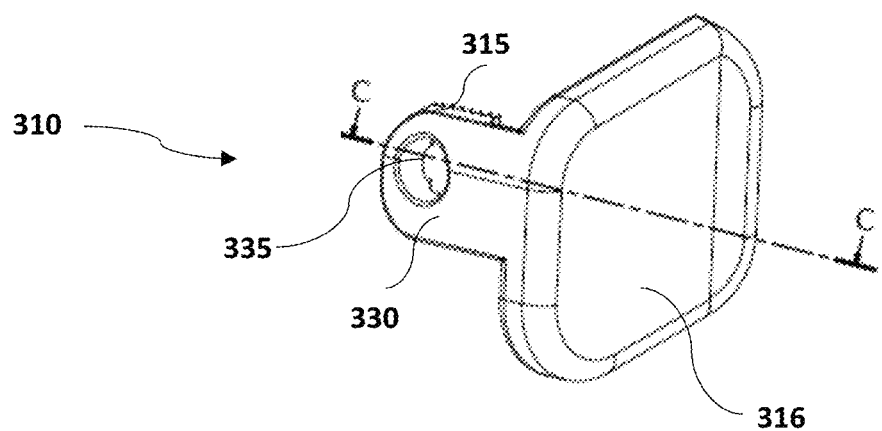
Figure 11D:
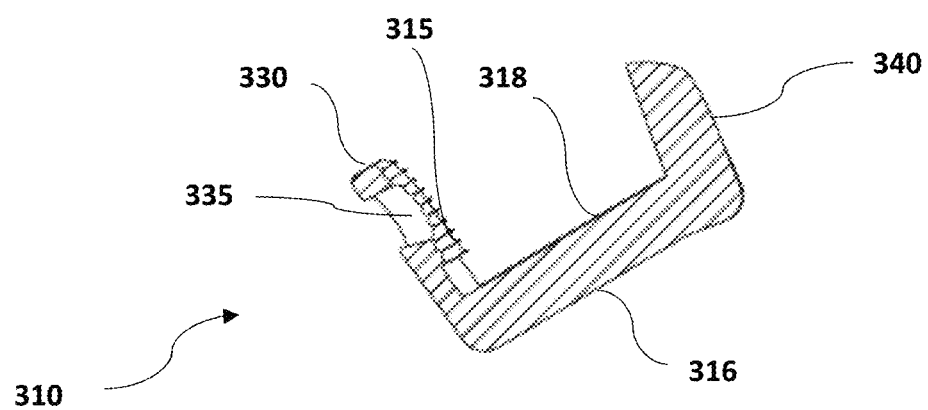

FIGS. 9A-C show details of the cover 210. Preferably the cover 210 is moulded as a single piece of thermoplastic polyurethane rubber, which is a biocompatible resilient material. Other materials may also be used so long as the cover 210 acts to buffer movement of the femur 10 relative to the pelvis 20 and particularly to the socket 25 thereby relieving pain from bone to bone contact.

In plan view, the cover 210 has a substantially lozenge shape substantially to match the shape of the cut surface 11 of the femur 10, although an oval shape similar to that of the cushion 110 in the first embodiment would also be possible. As shown in FIGS. 9A-C, apart from the flat bottom 218, the cover 210 has smooth surfaces all over to prevent sharp edges contacting the femur 10 or the pelvis 20 (including the socket 25) to minimise pain. The smooth surfaces of the cover 210 may include sections with different radii of curvature blended together or joined together by sections that are flat when viewed in one or more directions. The resulting smooth, low, rounded profile ensures the cover 210 can abut the outer rim of the socket 25 and allows it to move easily relative to the socket 25.

Instead of being fixed to the femur 10 by means of a bone screw 120 protruding into cut surface 11, the cover 210 is fixed by means of arms 230 and 240, which protrude downwards from the edges 224 on opposite sides of the upper part 214. In this embodiment, the arms 230, 240 are asymmetrically formed, with the outside arm 230 (on the laterally outer side when the prosthesis is fitted to the dog) extending a longer distance than the inside arm 240. Both arms 230, 240 are offset from the centre of the side 224 on which they are formed, with the outside arm 230 being offset further and formed closer to one of the corners 222 of the cover 210 than the inside arm 240. The inside arm 240 acts as a leading attachment arm and the outside arm 230 acts as an opposing attachment arm. This geometry provides more space for the vet or other suitably trained person to work with when fitting the prosthesis, and allows left and right-sided prostheses to be provided. However, this geometry is not essential and other acceptable geometries may be used.

The arms 230, 240 do not extend at right angles to the bottom surface 218 of the upper part 214 but instead a slightly obtuse angle to better fit the side of the femur 10. The arms 230, 240 are provided with respective arm holes 235, 245, whose centres are aligned with one another, for fixing the cover 210 to the femur 10 by means of a fixing means 250.

The fixing means 250 is shown in FIGS. 10A-D and comprises a retention pin 255 (FIG. 10A), an adapter sleeve 280 (FIGS. 10B and C) and a fixation wire 290 (FIG. 10D). The pin 250 includes a shaft 260, which preferably has smooth sides, with a stress relief adapter 270 at the proximal end and fixation holes 265 at the distal end. The tip at the distal end is rounded, or the edges at the tip are rounded to avoid sharp edges. The stress relief adapter 270 includes a plate 275 and a collar 272, which has wider diameter than the shaft 260. Each of the fixation holes 265 extends through the diameter of the shaft 260. In this embodiment, two fixation holes 265 are provided at different positions along the length of the shaft 260. However, it is possible to provide three or more fixation holes 265 or just one fixation hole 265.

The adapter sleeve 280 includes a plate 285 and collar 282 having the same outer diameter as the collar 272. A hole 287 sized to snugly fit the shaft 260 is formed through the plate 285 and the collar 282.

To fix the cover 210 to the femur 10, the vet or other suitably trained person first performs a femoral head and neck excision as described above. Subsequently, the vet drills a hole through the femur at a position corresponding to arm the holes 235, 245 in the arms 230, 240, the diameter of the hole corresponding to the outer diameter of the collars 272, 282. The vet then presses the bottom 218 of the upper part 214 against the cut surface 11, so the arm holes 235, 245 are aligned with the hole drilled through the femur, and slides the pin 255 through one of the arm holes 245 (235) (preferably the hole 245 in the inner/leading attachment arm 240) until the collar 272 fits snugly in the hole in the femur and the shaft 260 protrudes out the other side of the femur 10 and through the other arm hole 245 (235). Next, the vet slides the adapter 280 along the extending shaft 260 past at least one of the fixation holes 265 until the collar 282 is snugly fitted in the hole in the femur and the undersides of the respective plates 275, 285 abut the outside surfaces of their respective arms 230, 240. The vet then inserts the fixation wire 290 in the appropriate fixation hole 265, and twists and trims it.

As with the cushion 110 in the first embodiment, the cover 210 of this embodiment preferably comprises thermoplastic polyurethane rubber (TPU), or a similar a biocompatible resilient material. The preferred Shore A hardness of the material in this embodiment is 60-65. The material is chosen to have long-term in vivo biocompatibility, resistance to abrasion, shock and vibration damping, and flexural and tensile strength.

The cover 210 can take any suitable dimensions and proportions, with the arms 230, 240 extending any suitable distance downwards and the holes 235, 245 being positioned at an appropriate place and having an appropriate diameter. The cover 210 is sized and proportioned to fit the excision plane (cut surface 11). The upper part 214 of the cover 210 may have any appropriate thickness, so long as it provides a suitable buffer function. It may also have any suitable length and width. In the arrangement shown in FIGS. 8A and B, the cover 210 does not extend to the edges of the cut surface 11, but it may be sized to do so or even extend past the edges of the cut surface. Likewise, the pin 250 may have any appropriate length and diameter, as well as any appropriate number of fixation holes 265. As in the first embodiment, the prosthesis 200 can be provided in a range of sizes and the most appropriate size for the animal can be selected as necessary. Naturally, the size will be selected so that the arms 230, 240 are as closely spaced apart as the width of the femur 10 that will lie between them to ensure as close a fit as possible.

The angle between the arms 230, 240 and the bottom surface 218 is optimised for the morphology of a femur 10 of the type of animal in question. The arms 230, 240 are flexible enough to permit optimal conformation with the corresponding faces of the femur 10. By providing opposing arms 230, 240, they can be compressed against the sides of the femur 10 to hold the cover 210 in place.

The retention pin 255 is made of any suitable material that provides the required combination of material performance requirements including long-term in vivo biocompatibility, corrosion resistance, and flexural and tensile strength. The retention pin 255 may be made of or with implant grade titanium or may be made of or with polyether ether ketone (PEEK) or the like, which has a similar modulus to that of bone.

By providing the stress relief adapter 270 and the adapter sleeve 280, it is possible to increase the radius of the interface of the fixing means 250 with the femur 10 and hence to reduce the risk of stress failure during the life of the implant. In addition, the plate 285 on the adapter sleeve 280 provides a higher abrasion resistance than the arm 230 itself, thereby minimising wear between the fixation wire 290 and the cover 210.

By providing the different fixture holes 265, it is possible to adjust the compression between the attachment arms 230, 240 to a desired level.

The materials of the adapter sleeve 280 and the wire 290 are preferably matched to one another and to that of the retention pin 255 to minimise the risk of in vivo galvanic corrosion. The material of the wire 290 should also have suitable tensile and shear strengths in order to permit proper fixing of the cover 210 and minimise the risk of slippage of the pin 255 due to shear-induced wire failure. The wire should be flexible enough to conform to the particular morphology of the implant to allow proper fixing.

Preferably, when fitting the cover 210, the vet or other suitably trained person drills a hole in the femur 10 a little further down the stem of the femur 10 than the position of the holes 235, 245 when the cover 210 is first abutted against the cut surface 11 without applying any force. When the cover 210 is fitted, the upper part 214 is slightly compressed and the arms 230, 240 are extended until the position of the holes 235, 245 matches the position of the hole drilled in the femur 10. Due to their resilience, the arms 230, 240 and/or upper part 214 are consequently under a tensile force when fitted that acts to hold the cover 210 in place. The arms 230, 240 may be more or less flexible or pliant than the upper part 214.

Figure 12A:
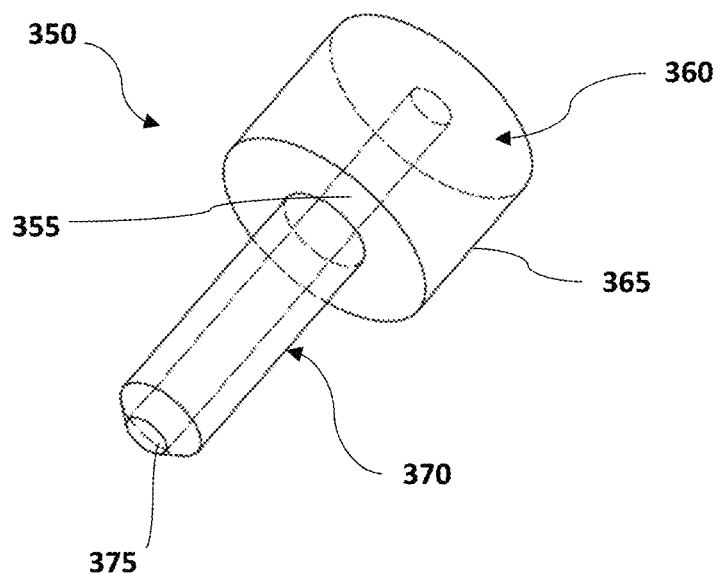
FIGS. 12A and 12B are perspective views of a drilling guide pin according to an aspect of the second embodiment-.
Figure 12B:
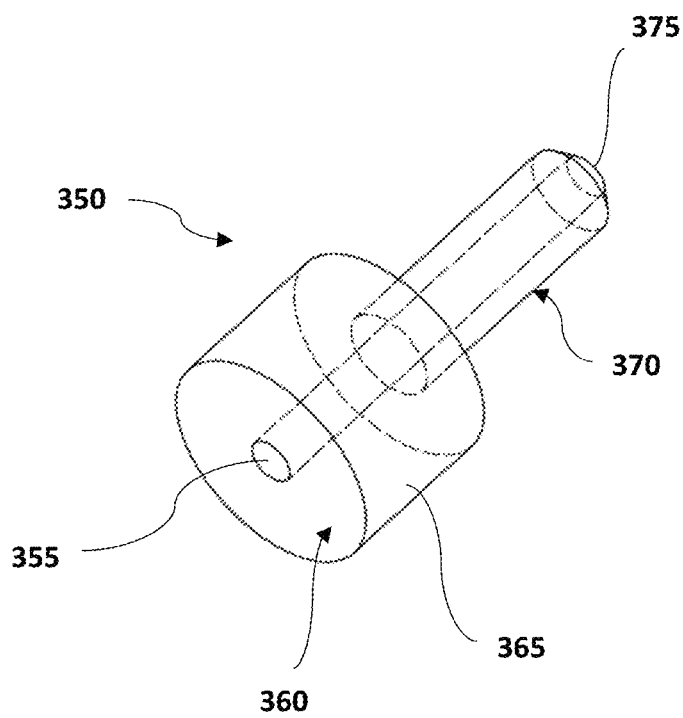

As noted above, fitting of the apparatus 200 requires the vet to drill a hole through the femur. Drilling the hole at the right position and angle is not a simple matter, but the position and angle of the hole should preferably be accurate to ensure proper fitting of the prosthesis 200. Accordingly, the present invention also provides a drill guide 300 as shown in FIGS. 11 and 12. In particular, the drill guide 300 includes a drill guide dummy 310 and a drill guide pin 350.

The drill guide dummy 310 is similarly shaped to the cover 210 and includes a dummy upper part 314 and dummy arms 330, 340. More particularly, the dummy guide arms include a leading dummy guide arm 340 and a far-side dummy guide arm 330. The leading dummy guide arm 340 includes a threaded hole 345, and the far-side dummy guide arm 330 includes a clearance hole 335. In addition, at least the far-side dummy guide arm 330 includes a serration feature 315 on its inner surface.

The drill guide pin 350 includes a head 360 and an externally threaded shaft 370. Preferably the head has a knurled side 365 to aid grip. A drill guide hole 355 extends through the head 360 and along the entire length of the shaft

370. The distal end of the drill guide hole 355 opens at the tip 375 of the shaft 370, which produces a sharp edge around the perimeter of the hole 355.

The drill guide dummy 310 is used to simulate the positioning of the cover 210 prior to drilling. The part has sharp corners only to the extent required to attach it to the femur head 10 during the fixation and drilling actions. All other corners are preferably rounded to avoid damage to soft tissue in the vicinity of the implantation site. The drill guide dummy 310 is made of a suitable material providing a combination of material performance requirements including superior corrosion resistance to withstand repeated sterilisation, bio-compatibility, and flexural and tensile strength to provide an adequate level of dimensional stability and rigidity during the drilling action.

To drill the hole in the femur, the vet positions the drill guide dummy 310 on the excision plane 11 to simulate the intended position of the cover 210. The vet then screws the threaded shaft 370 of the drill guide pin 350 into the threaded hole 345 of the leading dummy guide arm 340 until the sharp edge at the tip 375 bites into the bone, thereby pulling the two dummy guide arms 330, 340 together. The combination of the serration feature 315 on the inside of the far-side dummy guide arm 330, which abuts the femur 10, and the sharp edge at the tip 375 holds the assembled drill guide 300 in place on the femur 10. Subsequently, the vet inserts an appropriately sized drill bit through the drill guide hole 355 in the head 360 of the drill guide pin 350 and drills a hole through the femur 10 until the drill bit extends well past the clearance hole 335. In this way, a hole of substantially constant diameter can be cleanly drilled through the femur. Because the drill guide hole 355 extends through the head 360 and shaft 370 of the drill guide pin 350, which is firmly mounted to the femur 10 at the correct position, the drill guide 350 provides an accurate guide for drilling. Thus, the hole drilled in the femur 10 is at a position and angle that precisely corresponds with the intended mounting position of the cover 210.

The centres of the threaded hole 345 and the clearance hole 335 are further away from the underside 318 of the dummy upper part 314 than the centres of the holes 235, 245 are from the bottom 218 of the upper part 214 of the cover 210. In this way, when the cover 210 is mounted, in order to pass the pin 250 through the holes 235, 245 it is necessary to extend the arms 230, 240, thereby more tightly fixing the cover 210 in place, as discussed above.

The leading dummy guide arm 340, into which the drill guide pin 350 is screwed, possesses sufficient flexural strength to withstand the clamping pressure generated by the drill guide pin 350 during fixation of the drill guide dummy 310 and the drilling action.

The threaded hole 345 enables the application and retention of a clamping pressure between the tip 375 of the drill guide pin 350 and the femur bone during the fixation and drilling actions.

As noted above, the location of the threaded hole 345 is slightly offset from the location of the corresponding hole 245 on the cover 210 in order to generate tension in the leading arm 240 of the cover 210 when it is installed.

The far-side dummy guide arm 330 also possesses sufficient flexural strength to withstand the counter forces generated by the drill guide pin 350 and the leading arm 340 during fixation of the drill guide dummy 310 and the drilling action. The clearance hole 335 is large enough to permit clearance for a suitable drill bit during the drilling action. The centre of the clearance hole 335 is aligned with the centre of the threaded hole 345.

The serration feature 315 on the inner side of the far-side dummy guide arm 330 enables it to bite into the femur 10 during the fixation and drilling operation thus minimising the risk of the drill guide dummy 310 slipping and/or becoming detached from the femur 10 during the fixation and drilling actions.

The drill guide pin 350 is made of a suitable material providing a combination of material performance requirements including: superior corrosion resistance to withstand repeated sterilisation, bio-compatibility and tensile strength to provide an adequate level of dimensional stability and rigidity during the drilling action. The drill guide pin 350 is the compression force-generating element in the system. This enables the fixation of both the drill guide dummy 310 and the drill guide pin 350 to the femur 10 during the drilling action.

As with the first embodiment, the drill guide 250 may be provided separately or as part of a kit with the apparatus 200, with the components having corresponding sizes.

Accordingly, the present invention also provides a simple and effective apparatus and method for quickly and accurately drilling an appropriate hole in the femur 10 for fixing the apparatus 200 of the second embodiment. However, it will be appreciated that the use of the drill guide 300 described above is not essential for drilling the hole.

Accordingly, the second embodiment provides substantially the same advantages as the first embodiment. For example, the cover 210 is positioned between the cut surface 11 of the femur 10 and the socket 25. The cover 210 encounters the acetabular rim and pelvis, as shown in FIGS. 8A and B. Thus, it can be said that the cover 210 is disposed between the femur 10 and at least a part of the pelvis 20 around a hip socket 25. The basic biomechanics of the back leg and hip with the present invention are essentially the same as with a traditional femoral head and neck excision, but without the impediment of the bone to bone contact and excessive scar tissue formation. It will be understood therefore, that the cover 210 can likewise move away from the hip socket 25 and is not meant to engage it. Consequently, the cover 210 prevents bone to bone contact between the femur 10 and the pelvis 20, thereby significantly relieving pain compared both to the previously existing arthritic condition or other hip pathology and to the standard femoral head and neck excision. Because the cover 210 is formed of resilient material, such as thermoplastic polyurethane, this pain relieving effect of the present invention is a long-term one.

Moreover, the cover 210 prevents scar tissue from forming over the cut surface 11 and between the cut surface 11 and the pelvis 20 generally. This ensures that the range of movement of the joint does not become restricted with time following the operation. In particular, movement is constrained by the muscles and tendons only and not by the socket 25 or by scar tissue.

Consequently, the simple procedure of fitting the apparatus 200 of the present invention provides significantly improved pain relief and range of movement, both immediately after the operation and permanently after the operation, compared to carrying out only a femoral head and neck excision.

Moreover, the procedure of fitting the apparatus 200 of the second embodiment is as easy and quick (or more so) as the apparatus of the first embodiment 100. In addition, the apparatus of the second embodiment can provide a more secure fit with less biomechanical interference than the apparatus 100 of the first embodiment and can be expected to last longer. Consequently, the apparatus 200 of the second embodiment has the same advantages over performing a total hip replacement as discussed above, but with further improved results.

A third, more preferred embodiment of the invention will now be described with reference to FIGS. 13 and 14.

As in the first and second embodiments, in the third embodiment an apparatus is attached to a femur 10 that has undergone, for example, a femoral head and neck excision to provide the substantially planar surface 11. The apparatus 200 comprises a cover 500, which acts as the buffer, and a pin by which the cover 500 is mounted. The pin may be the same as the pin 250 used in the second embodiment, or it may a different pin. The cover 500 is entirely made of or includes a resilient material. The cover 500 is produced, sterilised and provided flat packed in the shape shown in FIG. 13. During the installation procedure the cover 500 is folded into its final shape, as shown in FIG. 14.

Figures 13A, 13B:
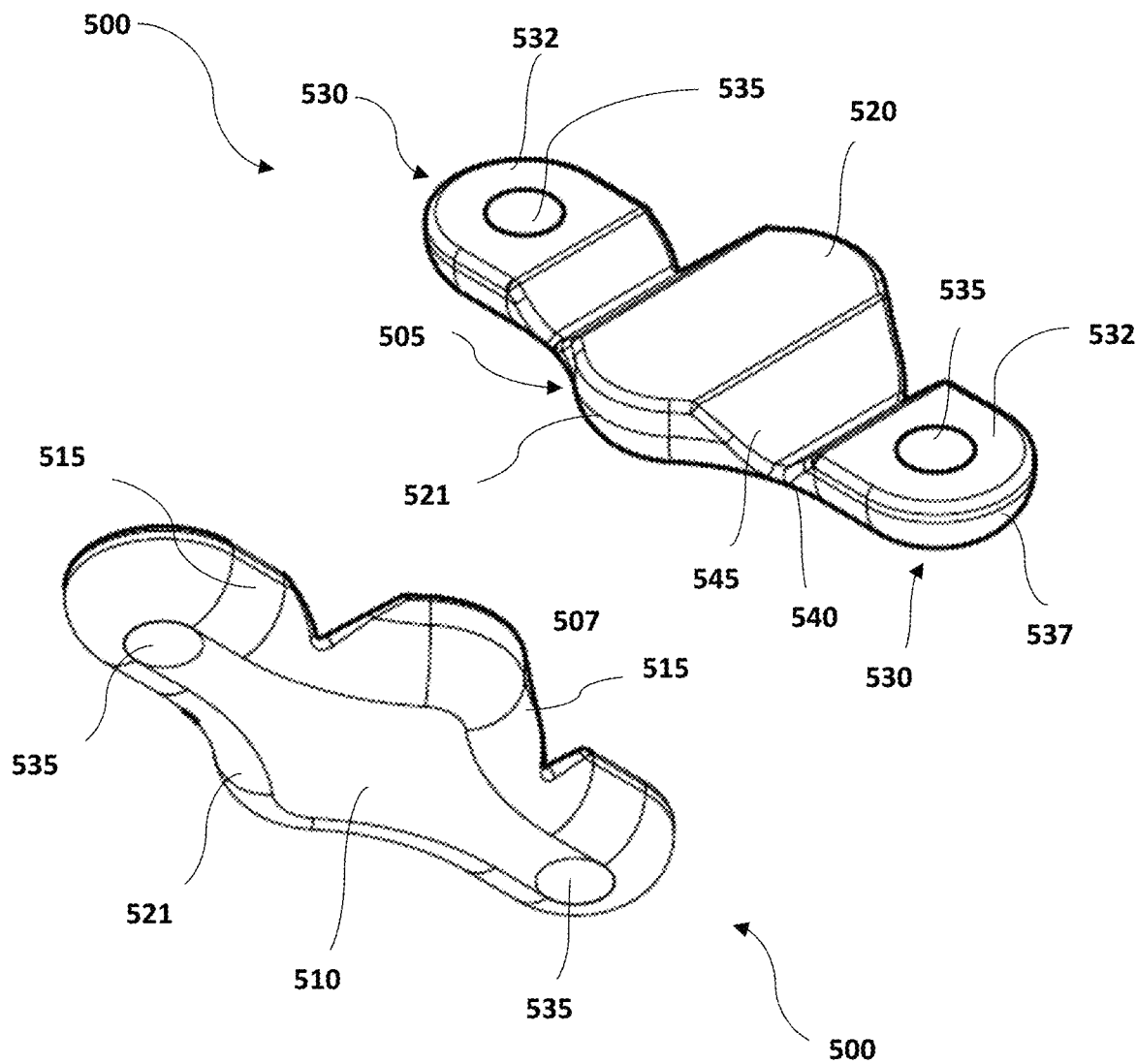
FIGS. 13A-D are views of a cover of the third embodiment before use.
Figure 13C:
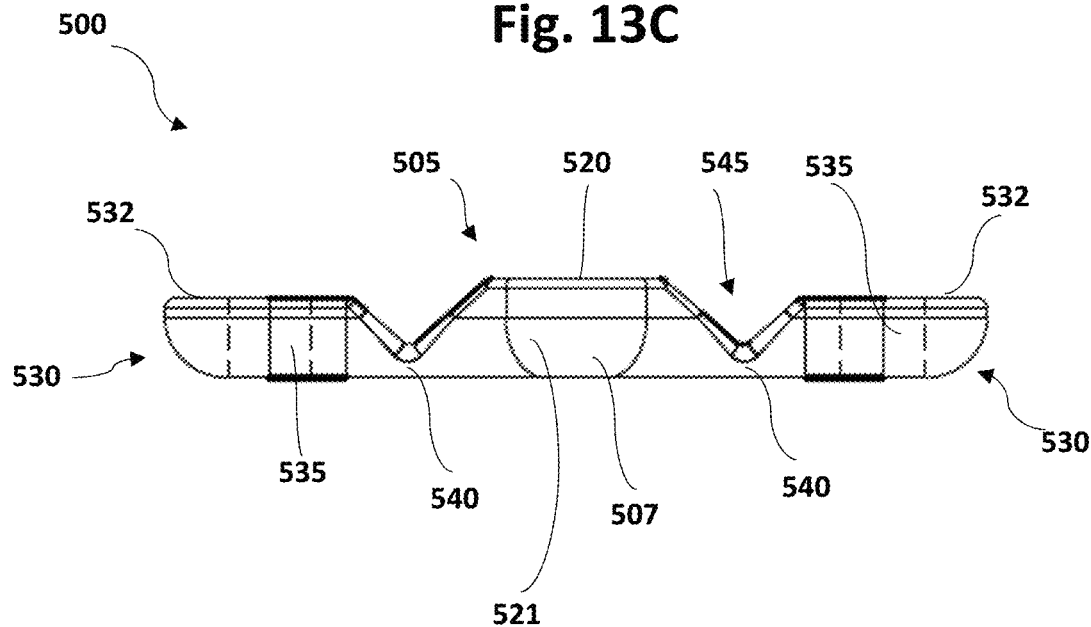
Figure 13D:
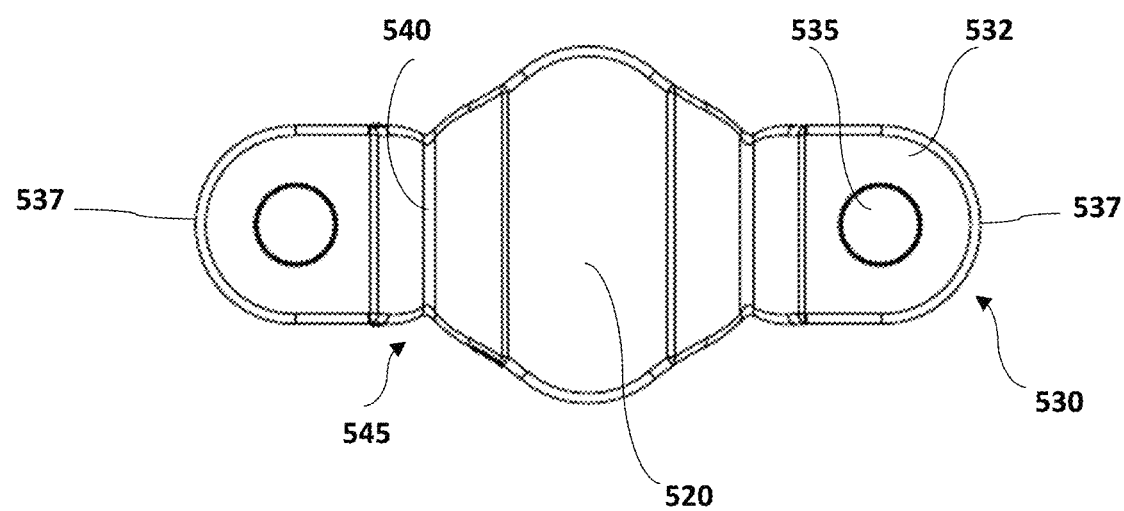

More specifically, FIG. 13A is a perspective view from above of the cover 500 opened out before use, FIG. 13B is a perspective view from below of the cover 500 opened out before use, FIG. 13C is a side view of the cover 500 opened out before use, and FIG. 13D is a plan view of the cover 500 opened out before use. In FIGS. 13A-D, the bottom is facing upwards.

Figures 14A, 14B:
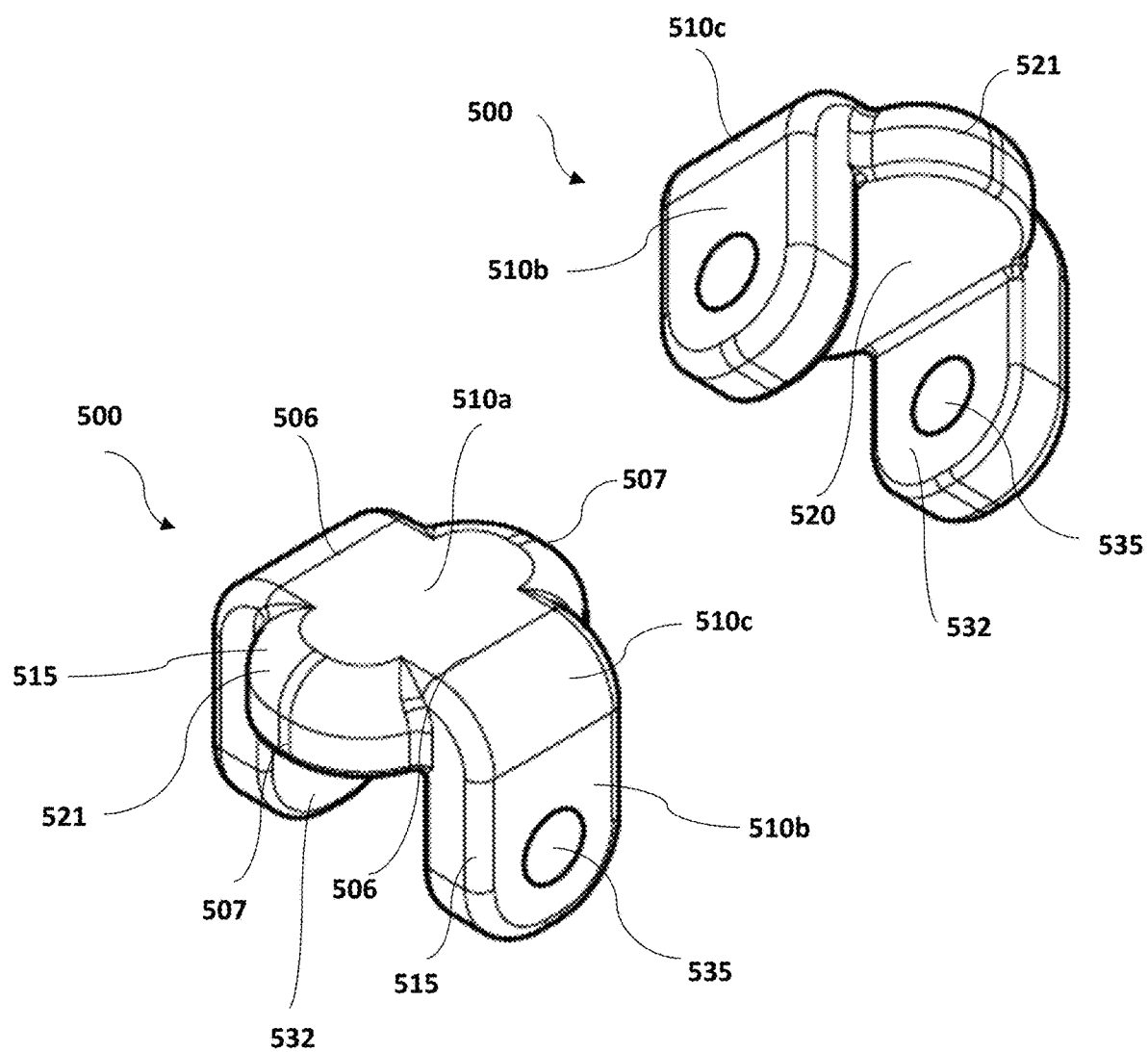
FIGS. 14A-D are views of the cover of the third embodiment with the arms bent into position for use.
Figure 14C:
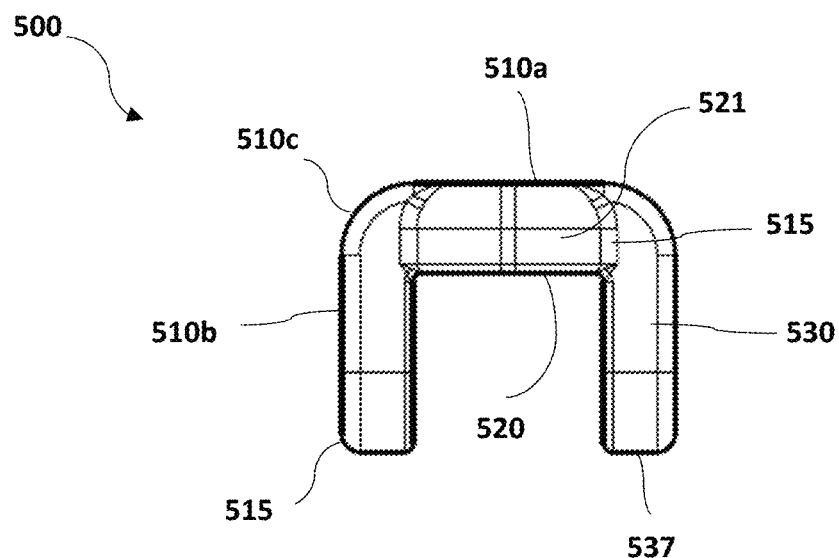
Figure 14D:
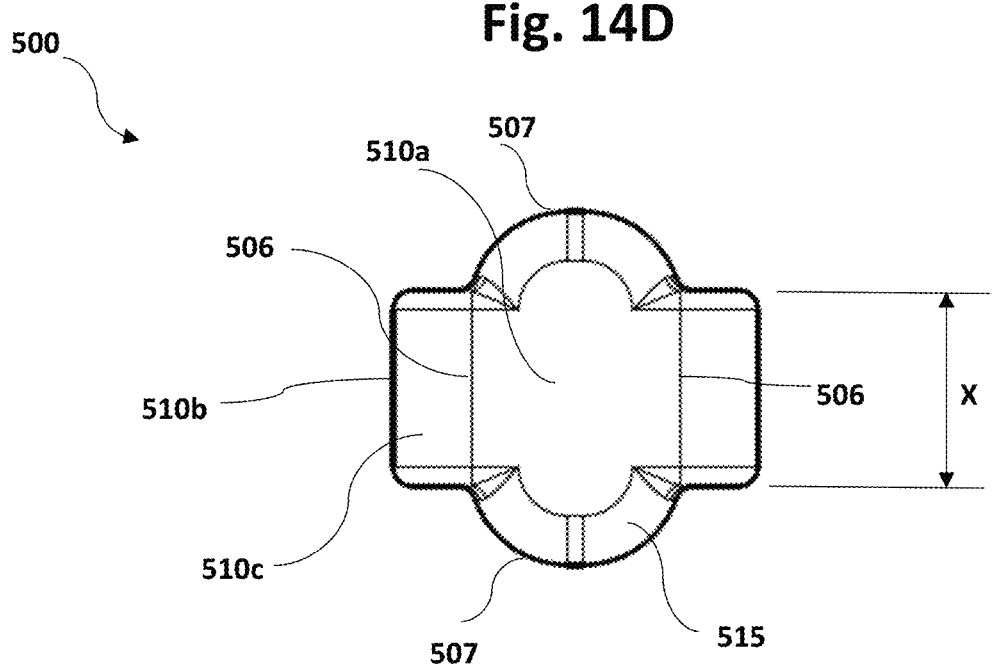

FIG. 14A is a perspective view from below of the folded cover 500, FIG. 14B is a perspective view from above of the folded cover 500, FIG. 14C is a side view of the folded cover 500, and FIG. 14D is a side view of the folded cover 500. In FIGS. 14A-D, the top is facing upwards.

As shown in FIG. 13, before use the cover 500 can be opened out and includes a main body 505 and arms 530 on opposite sides. The arms 530 are demarcated from the main body 505 by cut-out portions or grooves 545 in the cover 500 so that the arms 530 are attached to the main body 505 by living hinges 540. The main body 505 includes a bottom 520 and an upper part 521. A continuous surface 510, which is flat when the cover 500 is opened out, spans the upper part 521 of the main body 505 and the arms 530. The bottom 520 of the main body 505 is flat, as is the bottom or inner surface 532 of each of the arms 530. As best shown in FIG. 13C, the main body 505 is thicker than the arms 530 so that when the cover 500 is opened out and laid upside down on the upper surface 510, the bottom 520 of the main body 505 is higher than the bottom 532 of the arms 530.

In plan view from above, when the cover 500 is folded, the periphery of the main body 505 is akin to the shape of a running track with rounded ends 521 and imaginary flat sides 506 (parallel to the line of the living hinge 540), with blocks formed by the thickness of the adjacent the arms 530 extending outwards from the flat sides 506 (see FIG. 14D). It would be possible to use any other suitable shape, such as the oval shape of the first embodiment or the lozenge shape of the second embodiment. When folded, the arms 530 each have flat inner and outer sides 532, 510b extending downwards from the main body 505. The arms 530 have a distal rounded end 537. The continuous surface 510 is bent to form a flat upper surface 510a and flat side surfaces 510b (of the arms), which are joined by curved surfaces 510c in the vicinity of the living hinges 540.

The continuous surface 510 is joined to the bottom surface 520 of the main body 505 and the bottom or inner surface 532 of the arms 530 with curved surfaces 515 to provide a smooth, low profile. Thus, as shown in FIG. 14, when the cover 500 is folded and fitted, the cover 500 has smooth external surfaces all over to prevent sharp edges contacting the femur 10 or the pelvis 20 (including the socket 25) to minimise pain. The smooth surfaces of the cover 500 may include sections with different radii of curvature blended together or joined together by sections that are flat when viewed in one or more directions. The resulting smooth, low, rounded profile ensures the cover 500 can abut the outer rim of the socket 25 and allows it to move easily relative to the socket 25.

In use, the main body 505 acts a cushion and the bottom 520 of the main body 505 covers part (preferably all or most) of the planar surface 11 of the femur 10. This minimises the risk of damage to soft tissue in the vicinity of the cover 500.

The upper part 521 of the main body 505 abuts the outside of socket 25 of the pelvis 20. The main body 505 is dimensioned so that the largest dimension across in plan view when folded is larger than the largest dimension of the opening to the socket 25. Preferably, the main body 505 is sized so that its width and length in at least two orthogonal directions in plan view are larger than the diameter of the rim of the acetabular socket so that the rim or opening can be entirely covered by the cover 500. For example, in the exemplary embodiment it is preferred that both the largest distance 'x' between the rounded ends 507 as shown in FIG. 14D and the largest distance orthogonal to distance 'x' between the outer sides 510b of the arms 530 are both greater than the diameter of the opening to the socket. The upper part 521 of the main body 505 therefore it sits outside the socket 25 and contacts the rim of the acetabular socket 25 and pelvic bone 20 at various levels during weight bearing range of motion, similar to the manner shown in FIGS. 8A and 8B with respect to the second embodiment.

The provision of the buffer (in this embodiment in the form of a cover 500) between the cut surface 11 of the femur 10 and the existing hip socket 25 again prevents bone to bone contact, and in particular prevents the femur 10 from scraping the interior and the rim of the socket 25 or any other part of the pelvis 20, thereby significantly relieving pain and therefore enabling early return to function, which is critical in achieving a long-term good functional outcome. In addition, the provision of the buffer 500 reduces scar tissue formation, and this ensures that the range of motion of the femur 10 relative to the pelvis 20 does not become substantially restricted.

The implant 500 is made of a flexible, soft, resilient material. It provides flexibility for ease of installation as well as cushioning, high abrasion resistance and durability. The material is generally speaking a thermoplastic elastomer, preferably thermoplastic urethane and more preferably aromatic polyester thermoplastic urethane. The cover 500 may be produced via additive manufacturing or moulded as a single piece of the selected urethane, which is a biocompatible resilient material. Other materials may also be used so long as the cover 500 acts to buffer movement of the femur 10 relative to the pelvis 20 and particularly to the socket 25 thereby relieving pain from bone to bone contact. The preferred Shore A hardness of the material in this embodiment is 50-95, preferably 65-95 and more preferably 75-90. The material is chosen to have long-term in vivo biocompatibility, resistance to abrasion, shock and vibration damping, and flexural and tensile strength.

The living hinge 540 is designed to provide enough flexibility for ease of installation. The V-shaped cut-out 545 enables easy folding of the arms 530, ensuring that excess material is not compressed between the arm 530 and the cushion (main body 505) parts.

The cover 500 is fixed by means of the arms 530, in a similar manner to the cover 210 in the second embodiment. In this embodiment, the arms 530 are provided symmetrically on opposite sides of the main body. However, they may be provided asymmetrically similarly to the second embodiment. In this embodiment, both arms 530 are provided centrally, so that the cover 500 has two axes of symmetry when folded out, as show in FIG. 13D. However, one or both the arms 530 may be offset from the centre of the side on which they are formed, in similar manner to the second embodiment.

The angle of the faces of the cut-out 545 on either side of the hinge 545 is preferably approximately the same, and is designed so that the arms 530 can extend at about 90° to the bottom surface 530 of the main body 505. However, this angle is not fixed and a greater degree of folding may be allowed so that the cover 500 can be fitted to a wider range of sizes of femur. In addition, the angle may be slightly obtuse to better fit the side of the femur 10. The arms 530 are provided with respective arm holes 535, whose centres are aligned with one another when the cover is folded, for fixing the cover 500 to the femur 10 by means of a fixing means, such as fixing means 250 shown in FIGS. 10A-D. It will be appreciated that any other suitable fixing means may be used, such as a simple wire extending through a hole drilled in the femur and the arm holes 535, a nut and bolt, a pin with a screw head, a pin with a fixing wire passing through a hole at the end of the pin and so forth.

To fix the cover 500 to the femur 10, the vet or other suitably trained person first performs a femoral head and neck excision as described above. Subsequently, the vet drills a hole through the femur at a position corresponding to arm the holes 535 in the arms 530, the diameter of the hole corresponding to the outer diameter of the collars 272, 282 or other fixing means. The vet then presses the bottom 520 of the main body 505 against the cut surface 11, so the arm holes 535 are aligned with the hole drilled through the femur, and slides the pin 255 or other fixing means through one of the arm holes 535, through the hole in the femur and through the other arm hole 535, and then fixes it in place, for example using a nut, cap and/or fixation wire.

It is preferred that the distance from the excision surface 11 to the hole through the femur is greater than the distance from the bottom 520 of the main body 520 to the arm holes 532 when the cover 500 is folded to the extent that the faces of the V-shape groove meet and the cover 500 is otherwise at rest before fitting, the distances being orthogonal to the bottom 520 of the main body 505. As the cover 500 is being fitted, the main body 505 is slightly compressed and/or the arms 530 are slightly elongated so that the pin or other fixing means can fit through the arm holes 532 and the hole in the femur. Thus, after fitting is completed, the main body 505 remains compressed and/or the arms 530 remain stretched. The restoring force caused by the resilience of the elastic material used to form the cover presses the bottom 520 of the main body 505 and cut surface 11 of the femur 10 toward each other to hold the implant better in place. In the embodiment, the cover 500 is made of a unitary body and the restoring force is generated in the arms 530, the main body 505 and the living hinges 540. However, it is only necessary that one or more of these portions is formed of an elastic material to achieve the desired effect.

The cover 500 can take any suitable dimensions and proportions, with the arms 530 extending any suitable distance downwards and the holes 535 being positioned at an appropriate place and having an appropriate diameter. The cover 500 is sized and proportioned to fit the excision plane (cut surface 11). The main body 505 may have any appropriate thickness, so long as it provides a suitable buffer function. It may also have any suitable length and width. In the arrangement shown in FIGS. 13 and 14, the cover 210 is preferably sized to extend to or past the edges of the cut surface 11 in all directions, but it may be sized to do so only in some directions and need not do so at all. Dimensions similar to the first and second embodiments may be used.

The minimum thickness of the material at the trough 545 (that is, the minimum thickness of the living hinge 545) should be such that the material can provide enough stress strength to hold the implant in place for the service life. This thickness should be in the range of 0.5-4 mm, preferably 1.2-3 mm and more preferably 1.8-2.5 mm.

Likewise, the pin 250 or other fixing means may have any appropriate length and diameter, as well as any appropriate number of fixation holes 265.

As in the other embodiments, the prosthesis can be provided in a range of sizes and the most appropriate size for the animal can be selected as necessary. The size is selected so that the arms 530 are as closely spaced apart as the width of the femur 10 that will lie between them allows to ensure as close a fit as possible.

The angle between the arms 530 and the bottom surface 520 is optimised for the morphology of a femur 10 of the type of animal in question. The arms 530 are flexible enough to permit optimal conformation with the corresponding faces of the femur 10. By providing opposing arms 530, they can be compressed against the sides of the femur 10 to hold the cover 210 in place.

It will be appreciated by those skilled in the art that many modifications can be made to the apparatus 200 overall and/or any one or more of the individual components whilst still achieving the benefit of the invention.

All the modifications made to the second embodiment may also be made to the third embodiment.

For example, there is no need for whole cover 210, 500 to be formed of resilient material. Rather, the cover 210, 500 can be formed of different materials, only some of which are resilient and provide a cushioning effect. In this case, it is preferred that the parts of the buffer expected to abut bone, including the cut surface 11 and/or the rim of the socket 25 be formed of resilient or otherwise cushioning material. It is also possible to form the buffer 110, 210, 500 entirely of a rigid or substantially rigid material, such as PEEK or a thermoplastic like it. For example, the cover 210, 500 may comprise a rigid metal interior section covered by moulded resilient thermoplastic polyurethane (TPU). The arms 230, 240 may be formed of a different material, with different hardness/elasticity, to the upper part 214.

The shape of the cover 210, 500, including both the upper part 214, 521 and the arms 230, 240, 530 can be varied, as discussed above.

It is not necessary to provide either or both of the stress relief adaptor 270 and the adaptor sleeve 280. If omitted, a washer arrangement could be used instead.

The fixture holes 265 could be omitted and the adaptor sleeve 280 or a bolt could be screwed onto a threaded shaft 260 at either or both ends. The fixture holes 265 and wiring 290 could be used at either end of the shaft 260.

Alternatively, the cover 210, 500 could be fitted to the femur 10 by drilling pilot holes for each of the arm holes 235, 245, 535 of each of the inner and outer arms 230, 240, 530 and screwing a bone screw into each. Fixing could also be carried out using only one of the two arms.

The bottom 118, 218, 520 of the buffer 110, 210, 500 of any embodiment need not be flat, so long as it is possible to mount the cushion 110, 210 to the cut surface 11. The bottom 118, 218, 520 may be roughened instead of having a flat surface to assist with keying into the bone. Where circular sections are shown (in any embodiment), this is not essential.

The profile of the cushion 110 or cover 210, 500 can also be changed and need not be smooth all over. It may have a lower or higher profile, for example to reduce the shortening of the leg that is a side effect of a femoral head and neck excision.

In alternative embodiments, the face of the buffer 110, 210, 500 facing the pelvis may be flat, convex or concave. For example, buffer 110, 210, 500 may have a suction cup. In this case or for any previously described embodiment or variation, although other features of the invention may remain the same, the buffer 110, 210, 500 may instead be fixed to the femur using a hinged or universal joint for example, allowing one more directions of movement.

Any suitable material can be used for any of the components.

The components may have any suitable dimensions. Preferably, the dimensions explained above are used, within a margin of ±10%, or dimensions with these proportions.

The buffer 110, 210, 500 may be provided with a groove in which a metal ring is fitted to make the buffer visible to X-rays. Alternatively, the buffer 110, 210, 500 may include radiopaque material for this purpose. The same applies to the other components.

Both the bone screw 120 and the anchor screw 140 are shown as being fixed substantially at right angles to the cut surface 11. Similarly, the fixing pin 250 is shown as being horizontal to the cut surface 11. However, this is not essential and the angles can be changed. This can be achieved by changing the angle of the apertures 112, 114 where provided or of the holes 230, 240. The template or blind 150 and the drilling guide 350 may also be adjusted so the (pilot) hole(s) matches the angle of aperture(s).

It is also not essential for the various surfaces described as flat actually to be flat. Thus, the cut surface 11 need not be flat, nor need the bottom 118, 218, 520 of the cushion 110 or cover 210, 500 or the tops of the screw heads.

The foregoing description has been given by way of example only and it will be appreciated by a person skilled in the art that modifications can be made without departing from the scope of the present invention as defined by the claims.

The invention claimed is:

1. An apparatus for the treatment of a hip, the apparatus comprising:
   a main body adapted to be fitted to an excision surface of a femur from which at least the femoral head has been excised and to be disposed between a femur and at least a part of a pelvis around a hip socket; and
   arms having arm holes for attaching the arms to the sides of the femur,
   wherein the main body has a bottom surface and an upper part spaced in a first direction from the bottom surface, the bottom surface is adapted to abut the excision surface, a size of the main body in at least one direction in plan view is larger than a corresponding size of an opening of the acetabular socket of the hip subject to treatment, whereby the upper part contacts the rim of the acetabular socket and sits outside the acetabular socket allowing for movement of the upper part relative to the acetabular socket, and
   the arms are adapted to extend from the main body in a second direction away from the upper part and are positioned on opposite sides of a buffer.

2. An apparatus according to claim 1, wherein the upper part comprises a resilient material to abut at least a part of the pelvis around the hip socket.

3. An apparatus according to claim 1, wherein the upper part includes a substantially flat surface.

4. An apparatus according to claim 3, wherein a curved side surface joins the bottom surface and the flat surface of the upper part.

5. An apparatus according to claim 1, wherein the bottom surface of the buffer is substantially flat.

6. An apparatus according to claim 1, wherein the arms are connected to the buffer with a hinge such that the arms can be moved from a first position in which the apparatus is flat with the arms parallel to the buffer and a second position in which the apparatus is folded with the arms extending in the second direction away from the upper part.

7. An apparatus according to claim 6, wherein the buffer and arms are formed with a unitary body of a resilient material and the hinge is a living hinge.

8. An apparatus according to claim 7, wherein the living hinge is formed by a groove between the buffer and the arms.

9. An apparatus according to claim 6, wherein the upper part and an outer surface of the arms form a continuous flat surface in the first position.

10. An apparatus according to claim 1, wherein an axis of the arm holes of the arms extending from the buffer in the second direction away from the upper part is substantially parallel to the bottom surface.

11. An apparatus according to claim 1, wherein a width and length of the buffer in plan view are larger than corresponding dimensions of the opening of the acetabular socket.

12. An apparatus according to claim 1, wherein a perimeter of the buffer is larger than a perimeter of the acetabular socket.

13. An apparatus according to claim 1, further comprising a fixing means for extending between the arm holes through a hole provided in the femur.

14. An apparatus according to claim 13, wherein the fixing means is a (Original) pin with at least one fixing hole extending through the pin at an angle to the longitudinal axis of the pin, the at least one fixing hole being provided towards a distal end of the pin.

15. An apparatus according to claim 14, further comprising a sleeve adapted to fit over the distal end of the pin.

16. An apparatus according to claim 15, wherein the sleeve has a plate-like portion suitable for being interposed between a fixing wire and the femur.

17. An apparatus according to claim 14, wherein a proximal end of the pin has a larger diameter than a shaft of the pin.

18. An apparatus according to claim 14, further comprising a plate like portion at a proximal end of the pin and arranged to abut the femur when the apparatus is mounted to the femur.

* * * * *